(12) United States Patent
Aikawa

(10) Patent No.: US 11,703,456 B2
(45) Date of Patent: Jul. 18, 2023

(54) COMPONENT MEASUREMENT DEVICE AND COMPONENT MEASUREMENT DEVICE SET

(71) Applicant: TERUMO KABUSHIKI KAISHA, Tokyo (JP)

(72) Inventor: Ryokei Aikawa, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 858 days.

(21) Appl. No.: 16/575,137

(22) Filed: Sep. 18, 2019

(65) Prior Publication Data

US 2020/0011806 A1 Jan. 9, 2020

Related U.S. Application Data

(63) Continuation of application No. PCT/JP2018/006338, filed on Feb. 22, 2018.

(30) Foreign Application Priority Data

Mar. 23, 2017 (JP) ................................. 2017-057385

(51) Int. Cl.
*G01N 21/78* (2006.01)
*G01N 33/66* (2006.01)
*G01N 21/77* (2006.01)

(52) U.S. Cl.
CPC ............. *G01N 21/78* (2013.01); *G01N 33/66* (2013.01); *G01N 2021/7763* (2013.01); *G01N 2021/7783* (2013.01)

(58) Field of Classification Search
CPC ........ G01N 33/66; G01N 21/77; G01N 21/78; G01N 2021/7763; G01N 2021/7783;
(Continued)

(56) References Cited

U.S. PATENT DOCUMENTS 6,018,607 A   1/2000   Schwarz
6,707,554 B1  3/2004   Miltner et al.
(Continued)

FOREIGN PATENT DOCUMENTS

CN   103429154 A    12/2013
EP   1 528 380 A1    5/2005
(Continued)

OTHER PUBLICATIONS

Office Action dated Oct. 8, 2021 issued in a corresponding Chinese Patent Application No. 201880020281.3, (22 pages).
(Continued)

*Primary Examiner* — Jennifer Wecker
*Assistant Examiner* — Michelle Adams
(74) *Attorney, Agent, or Firm* — Foley & Lardner LLP

(57) ABSTRACT

A component measurement device for measuring a component of interest in blood on a basis of optical characteristics of a mixture containing a color component produced by a color reaction between the component of interest in the blood and a reagent includes: a first light source configured to emit first irradiation light of a first predetermined wavelength to the mixture; and a second light source configured to emit second irradiation light of a second predetermined wavelength to the mixture, the second irradiation light to be used for estimation of a noise amount contained in a measured value of absorbance of the mixture measured by using the first irradiation light of the first light source, the noise amount being derived other than from the color component.

11 Claims, 18 Drawing Sheets

(58) Field of Classification Search
CPC ....... G01N 21/3151; G01N 2201/0627; G01N 2021/3129; G01N 2021/3133; G01N 2021/3137
See application file for complete search history.

(56) References Cited

U.S. PATENT DOCUMENTS

| | | | | |
|---|---|---|---|---|
| 2010/0259747 | A1* | 10/2010 | Sekimoto | G01N 21/8483 356/213 |
| 2011/0026029 | A1* | 2/2011 | Iwasaki | G01N 21/359 356/417 |
| 2017/0010273 | A1* | 1/2017 | Takinami | A61B 5/150022 |
| 2019/0049468 | A9* | 2/2019 | Ochiai | C12Y 111/01 |
| 2020/0340888 | A1* | 10/2020 | Moriuchi | G01N 21/78 |

FOREIGN PATENT DOCUMENTS

| | | |
|---|---|---|
| EP | 2 408 931 A2 | 1/2012 |
| JP | 07-034758 B2 | 4/1995 |
| JP | 2002-525625 A | 8/2002 |
| JP | 2010-281751 A | 12/2010 |
| JP | 2015-179038 A | 10/2015 |
| WO | WO-2013/146065 A1 | 10/2013 |
| WO | WO-2015/137074 A1 | 9/2015 |
| WO | WO-2015/146238 A1 | 10/2015 |
| WO | WO-2017/154270 A1 | 9/2017 |
| WO | WO-2019138681 A1 * 7/2019 ......... A61B 5/14532 |

OTHER PUBLICATIONS

Extended European Search Report dated Dec. 3, 2020 in corresponding European Patent Application No. 18770280.8.
International Searching Authority, "International Search Report," issued in connection with International Patent Application No. PCT/JP2018/006338, dated May 1, 2018.
International Searching Authority, Written Opinion, issued in connection with International Patent Application No. PCT/JP2018/006338, dated May 1, 2018.

* cited by examiner

FIG.8
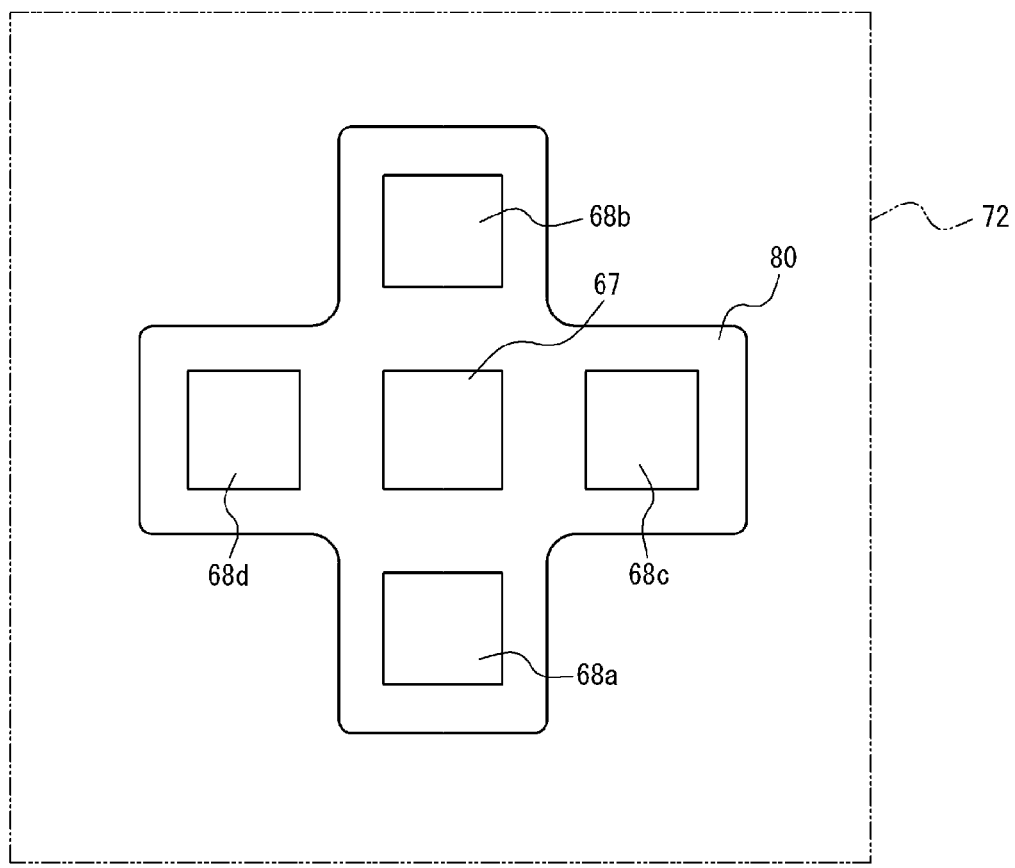
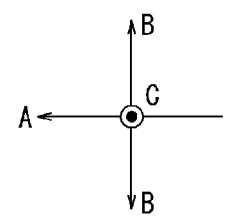

COMPONENT MEASUREMENT DEVICE AND COMPONENT MEASUREMENT DEVICE SET

CROSS-REFERENCE TO RELATED APPLICATIONS

This is a bypass continuation of PCT Application No. PCT/JP2018/006338, filed on Feb. 22, 2018, which claims priority to Japanese Application No. 2017-057385, filed on Mar. 23, 2017. The contents of these applications are hereby incorporated by reference in their entireties.

BACKGROUND

The present disclosure relates to a component measurement device and a component measurement device set.

BACKGROUND ART

In the biochemical field and the medical field, conventionally, the following technique has been known as a method for measuring a component of interest contained in blood (whole blood) or a sample. That is, blood is separated into a part containing a component of interest and a part without the component of interest so as to measure an amount or a concentration of the component of interest. For example, in a known technique for measuring a glucose concentration (mg/dL, mmo/L) in plasma, a plasma component is separated from blood with a filter or the like, so that the glucose concentration in plasma can be measured.

However, it is difficult to thoroughly separate the plasma component in the blood in a short time. In addition, there are variations in the performance of the filter or the like used for the separation, so that a hemocyte component would be partially contained in the separated plasma component. Therefore, it is difficult to measure the glucose concentration precisely. Besides, there is known a method for measuring a glucose concentration after hemolysis of blood, as disclosed in Japanese Pat. No. JP H07-34758 B. However, similar to the above-described plasma separation, it is time-consuming to hemolyze the blood, and a hemocyte component would remain in a post-hemolysis liquid.

On the other hand, whole blood measurement by absorption photometry is known as one method for measuring a component of interest in blood without separation of the component of interest from the blood and without hemolysis of the blood. According to this method, the time required for measuring the component of interest is reduced, as compared with the method involving the step of separating the component of interest or the step of hemolysis. However, when a large amount of component other than the component of interest is contained in the blood, the other component would cause optical phenomena such as light absorption or light scattering, thereby acting as a disturbance factor (noise) in measurement. In order to maintain accuracy in measuring the component of interest, it is required to remove the influence of this disturbance factor. In order to remove the influence of the disturbance factor, various methods have been proposed.

PCT Pub. No. WO 2015/137074 A discloses a component measurement device and a component measurement method in which a degree of influence of a disturbance factor at a measuring wavelength is estimated from values measured at long wavelength bands (that is, wavelength bands longer than the measuring wavelength), and a measured value at the measuring wavelength is corrected based on the estimated degree of influence of the disturbance factor, and the measured value at the measuring wavelength is further corrected based on a predicted hematocrit level, thereby working out a glucose concentration in a plasma component. Furthermore, PCT Pub. No. WO 2015/137074 A discloses that various light emitting elements such as Light Emitting Diode (LED) elements, organic Electro-Luminescence (EL) elements, inorganic EL elements, and Laser Diode (LD) elements are usable as plural kinds of light sources.

SUMMARY

According to the component measurement device and the component measurement method disclosed in PCT Pub. No. WO 2015/137074 A, a glucose concentration in a plasma component can be measured from blood with high accuracy without separating from the blood the plasma component containing glucose, that is, the component of interest to be measured. However, in the case in which a plurality of light sources different in their peak wavelength is used, there would occur differences in measuring position of the component interest depending on the light sources. Such differences in measuring positions would possibly reduce measurement accuracy of the measurement of the component of interest in the blood.

An object of the present disclosure is to provide a component measurement device and a component measurement device set, which are so configured that measurement accuracy is unlikely reduced even if a plurality of light sources are used.

A component measurement device according to a first aspect of the present invention is for measuring a component of interest in blood on the basis of optical characteristics of a mixture containing a color component produced by a color reaction between the component of interest in the blood and a reagent. The component measurement device including: a first light source configured to emit irradiation light of a first predetermined wavelength to be emitted to the mixture; and a second light source configured to emit irradiation light of a second predetermined wavelength to be emitted to the mixture and to be used for estimation of a noise amount contained in a measured value of absorbance of the mixture measured by using the irradiation light of the first light source, the noise amount being derived other than from the color component, in which the first light source and the second light source are aligned in a flow path width direction perpendicular to a flow direction of the blood at a position where the mixture is present in a flow path of the blood.

In an embodiment, a first irradiation position and a second irradiation position on the mixture at least partially overlap with each other in the flow path width direction, where the irradiation light of the first light source irradiates the first irradiation position on the mixture and the irradiation light of the second light source irradiates the second irradiation position on the mixture.

The component measurement device according to an embodiment further includes a third light source configured to emit irradiation light of a third predetermined wavelength to be emitted to the mixture and to be used for the estimation of the noise amount, in which the first light source, the second light source, and the third light source are aligned in the flow path width direction with the first light source positioned in a middle of these light sources.

In an embodiment, the first irradiation position and a third irradiation position at least partially overlap with each other in the flow path width direction, where the irradiation light of the third light source irradiates the third irradiation position on the mixture.

In an embodiment, the second irradiation position and the third irradiation position at least partially overlap with each other in the flow path width direction.

The component measurement device according to an embodiment further includes a fourth light source configured to emit irradiation light of a fourth predetermined wavelength to be emitted to the mixture and to be used for the estimation of the noise amount, in which the first light source and the fourth light source are aligned in the flow direction.

The component measurement device according to an embodiment further includes a fifth light source configured to emit irradiation light of a fifth predetermined wavelength to be emitted to the mixture and to be used for the estimation of the noise amount, in which the first light source, the fourth light source, and the fifth light source are aligned in the flow direction with the first light source positioned in the middle of these light sources.

The component measurement device according to an embodiment further includes a light receiving unit positioned to face the first light source and the second light source with the mixture between the light receiving unit and the first and second light sources when the mixture is present in the flow path, the light receiving unit being configured to receive transmitted light, which is that part of the irradiation light of the first and second light sources that has been transmitted through the mixture; and a diaphragm unit positioned to be between the mixture and the light receiving unit, and configured to control how much of the transmitted light that has been transmitted through the mixture reaches the light receiving unit.

The component measurement device according to an embodiment further includes a second diaphragm unit positioned to be between the mixture and the first and second light sources, and configured to control how much light reaches from the first light source and the second light source to the mixture, in which the diaphragm unit is referred to as a first diaphragm unit.

The component measurement device according to an embodiment is configured to receive a component measurement chip attachable to and detachable from the component measurement device. The component measurement chip is configured to define the flow path. The first light source and the second light source are aligned in the flow path width direction when the component measurement chip is attached to the component measurement device.

A component measurement device set according to a second aspect of the present invention includes: a component measurement chip being configured to define a flow path for a flow of blood, and being provided with a reagent in the flow path, the reagent containing a coloring reagent for causing a color reaction with a component of interest in the blood so as to produce a color component; and a component measurement device configured to receive the component measurement chip, and to measure the component of interest in the blood on the basis of optical characteristics of a mixture containing the color component produced in the flow path by the color reaction, the component measurement device including: a first light source configured to emit irradiation light of a first predetermined wavelength to be emitted to the mixture in the flow path of the component measurement chip attached to the component measurement device; and a second light source configured to emit irradiation light of a second predetermined wavelength to be emitted to the mixture in the flow path of the component measurement chip attached to the component measurement device, and to be used for estimation of a noise amount contained in a measured value of absorbance of the mixture measured by using the irradiation light of the first light source, the noise amount being derived other than from the color component, in which the first light source and the second light source are aligned in a flow path width direction perpendicular to a flow direction of the blood at a position where the mixture is present in the flow path of the component measurement chip attached to the component measurement device.

According to the present disclosure, it becomes possible to provide a component measurement device and a component measurement device set that are configured so that measurement accuracy is unlikely to be reduced even if a plurality of light sources are used.

BRIEF DESCRIPTION OF THE DRAWINGS

FIG. 8 is a view illustrating positional relationships of a plurality of light sources in the component measurement device illustrated in FIG. 1.

DETAILED DESCRIPTION

Figure 1:
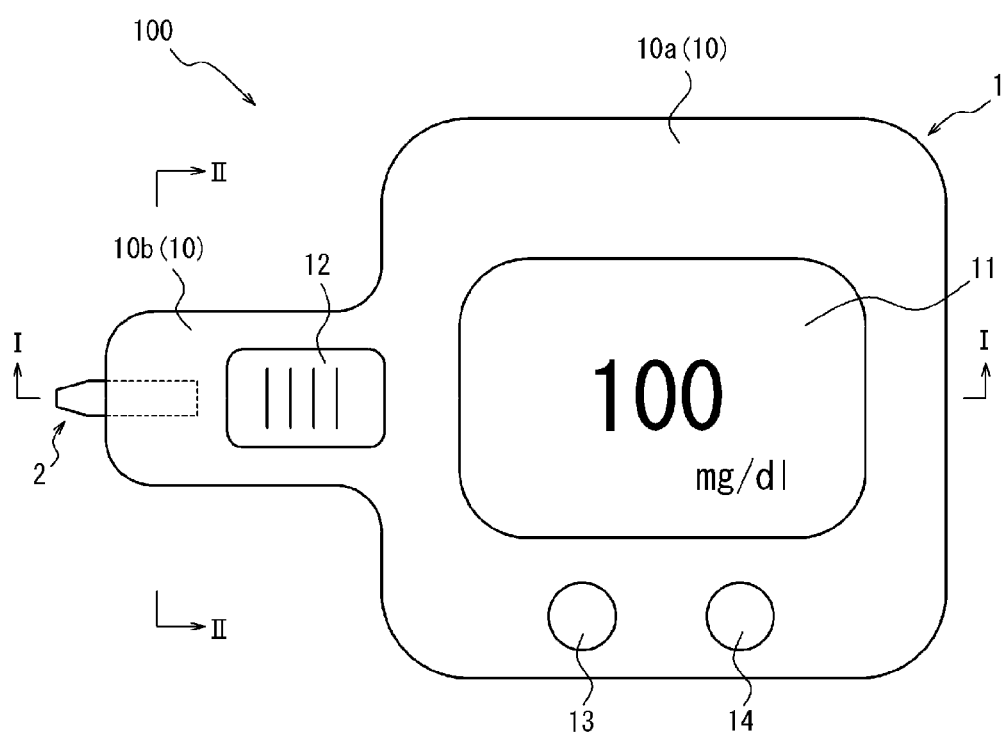
FIG. 1 is a top view of a component measurement device set in which a component measurement chip is attached to a component measurement device according to an embodiment.

In the following, embodiments of a component measurement device and a component measurement device set according to the present disclosure will be described, referring to FIGS. 1 to 19. In the drawings, like members are labeled with like reference symbols.

Figure 2:
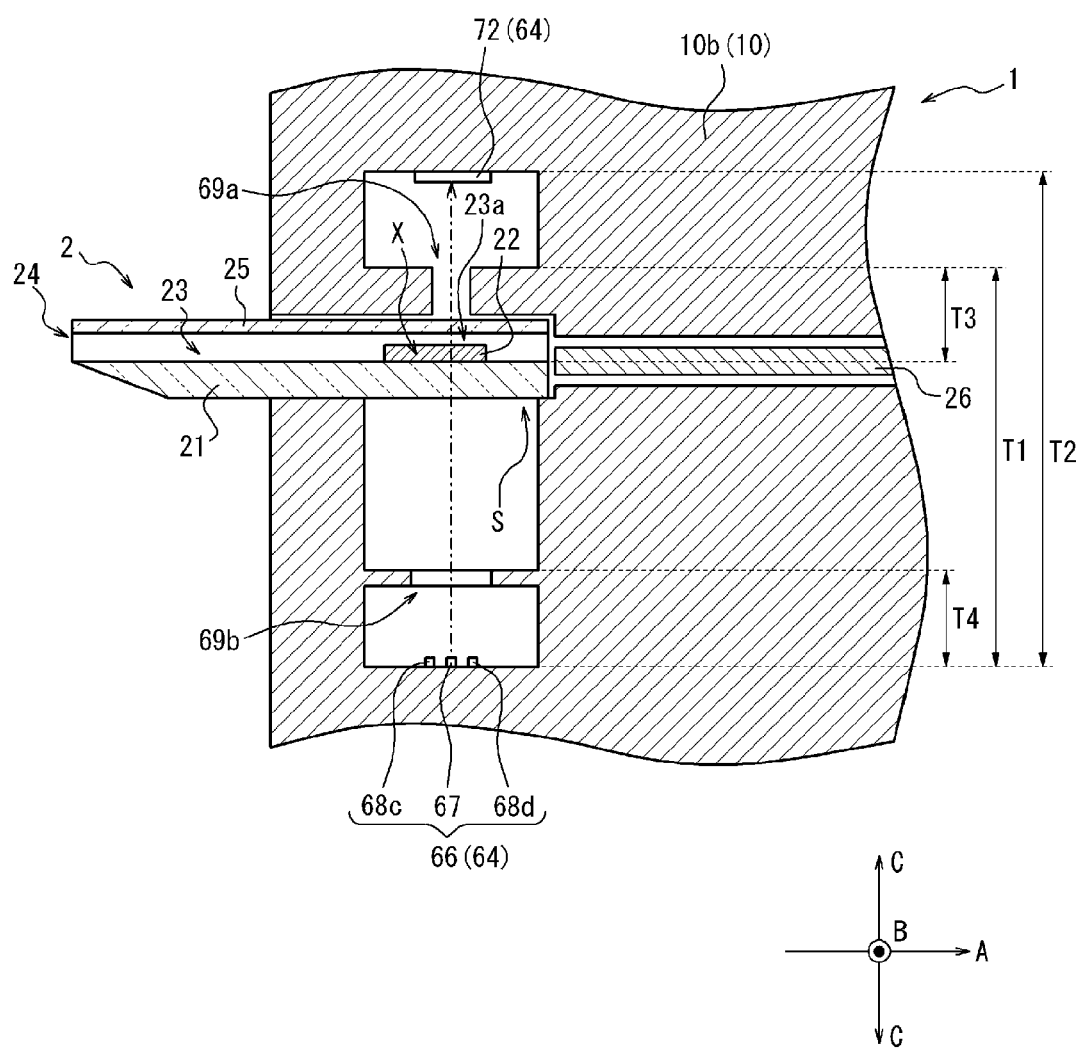
FIG. 2 is a view illustrating a cross section along I-I in FIG. 1.
Figure 3:
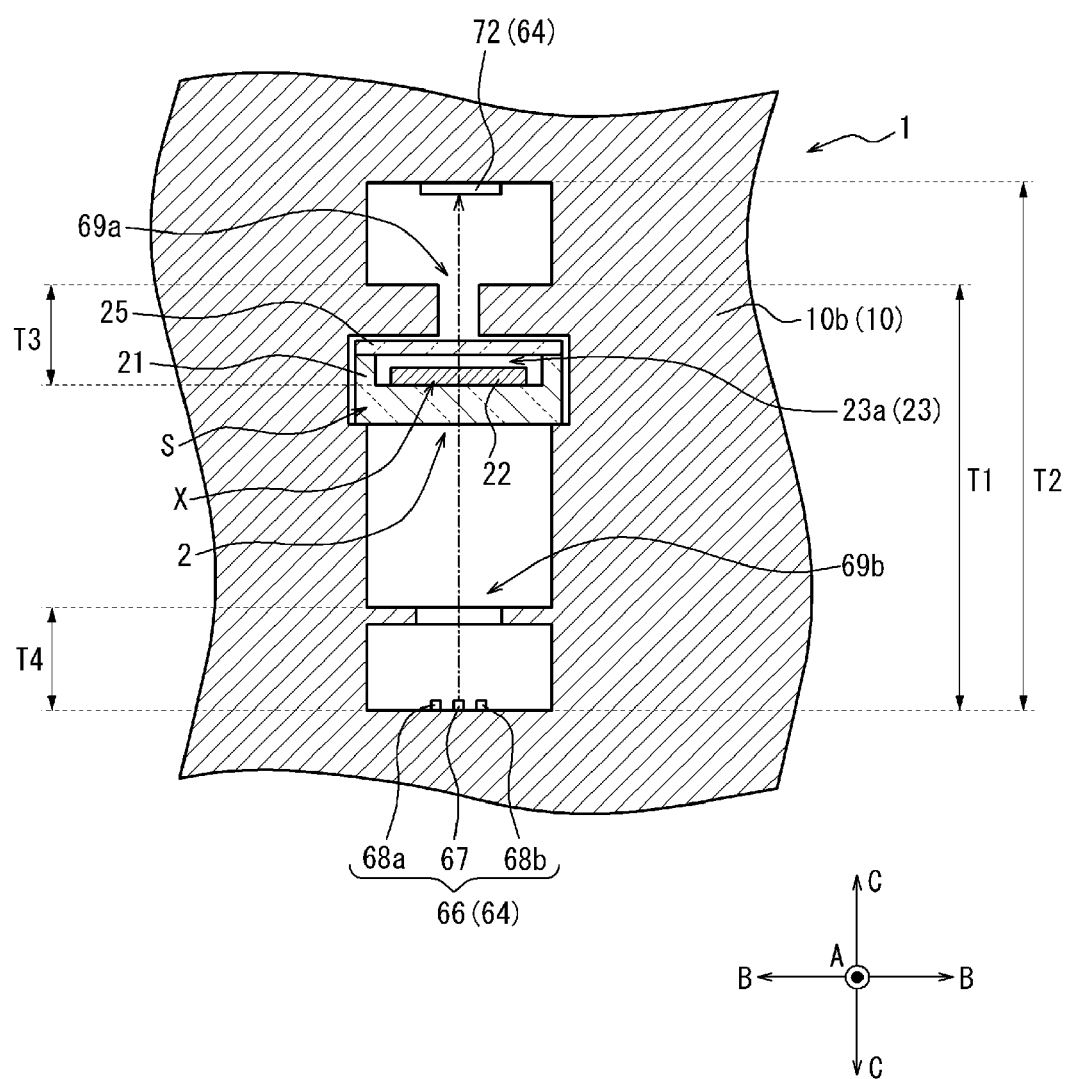
FIG. 3 is a view illustrating a cross section along II-II in FIG. 1.

To begin, one embodiment of a component measurement device according to the present disclosure will be described. FIG. 1 is a top view of a component measurement device set 100 in which a component measurement chip 2 is attached to a component measurement device 1 according to this embodiment. FIG. 2 is a cross sectional view illustrating a cross section along I-I in FIG. 1. FIG. 3 is a cross sectional view illustrating a cross section along II-II in FIG. 1. FIGS. 2 and 3 illustrate, in an enlarged manner, a vicinity in which the component measurement chip 2 is attached.

As illustrated in FIGS. 1 to 3, the component measurement device set 100 includes the component measurement device 1 and the component measurement chip 2. The component measurement device 1 of this embodiment is a blood glucose level measurement device capable of measuring a glucose concentration in a plasma component as a component of interest to be measured in blood. The component measurement chip 2 of this embodiment is a blood glucose level measurement chip that is attachable to a tip of the blood glucose level measurement device serving as the component measurement device 1. It should be noted that the term "blood" herein represents whole blood that has not been separated into components, and therefore includes all components.

The component measurement device 1 is provided with a housing 10 made from a resin material; a button group provided on an upper surface of the housing 10; a display unit 11 provided on the upper surface of the housing 10, the display unit 11 including a liquid crystal, or light emitting diodes (LEDs) or the like; and a detachment lever 12 for use in detaching the component measurement chip 2 from the component measurement device 1 to which the component measurement chip 2 is attached.

The button group of this embodiment includes a power button 13, and an operation button 14.

As illustrated in FIG. 1, the housing 10 includes a main body 10a and a chip attaching portion 10b. The main body 10a has a substantially rectangular outline as viewed from the top, and the button group and the display unit 11 are provided on an upper surface of the main body 10a. The chip attaching portion 10b protrudes outward from the main body 10a, and the detachment lever 12 is provided on an upper surface of the chip attaching portion 10b. As illustrated in FIG. 2, a chip attaching space S is defined inside the chip attaching portion 10b in such a way that one end of the chip attaching space S opens on a surface of a tip of the chip attaching portion 10b, thereby forming a tip opening. To attach the component measurement chip 2 to the component measurement device 1, the component measurement chip 2 is inserted into the chip attaching space S from the outside through the tip opening, and the component measurement chip 2 is pushed until it reaches a predetermined position, so that the component measurement chip 2 is engaged on the chip attaching portion 10b of the component measurement device 1. As a result, the component measurement chip 2 is attached to the component measurement device 1. The component measurement chip 2 may be engaged on the component measurement device 1 by various configurations. For example, a claw that is engageable with a part of the component measurement chip 2 may be provided inside the chip attaching portion 10b.

To detach the component measurement chip 2 attached to the component measurement device 1 from the component measurement device 1, the above described detachment lever 12 is handled from the outside of the housing 10 to disengage the component measurement chip 2 from the chip attaching portion 10b of the component measurement device 1. At the same time, an ejector pin 26 (see FIG. 2) inside the housing 10 moves in tandem with the disengagement, thereby allowing the component measurement chip 2 to be detached from the component measurement device 1.

The housing 10 of this embodiment is not limited to the shape of this embodiment in which the housing 10 has the main body 10a having a substantially rectangular shape as viewed from the top (see FIG. 1), and the chip attaching portion 10b protruding outward from the main body 10a, and the housing 10 may have any shape as long as the housing 10 includes a chip attaching portion to which the component measurement chip 2 is attachable. Therefore, besides the shape of the housing 10 of this embodiment, various other shapes that enable a user to grasp the housing 10 with one hand are employable.

The display unit 11 can display information on the component of interest measured by the component measurement device 1. In this embodiment, the glucose concentration measured by the blood glucose level measurement device, that is the component measurement device 1, can be displayed on the display unit 11. It should be noted that the display unit 11 may display not only the information on the component of interest but also various kinds of information such as measurement conditions of the component measurement device 1 and instruction information instructing a user to do a predetermined operation. The user can operate the power button 13 or the operation button 14 of the button group, while referring to the contents displayed on the display unit 11.

Furthermore, as illustrated in FIGS. 2 and 3, the component measurement device 1 includes a light emitting unit 66 and a light receiving unit 72. The light emitting unit 66 and the light receiving unit 72 are so arranged that they face each other with the chip attaching space S positioned therebetween. As illustrated in FIGS. 2 and 3, in a state where the component measurement chip 2 is mounted in the chip attaching space S of the component measurement device 1, irradiation light emitted from the light emitting unit 66 will be emitted to the component measurement chip 2. The light receiving unit 72 is configured to receive transmitted light, which is that portion of the irradiation light that has been transmitted through the component measurement chip 2 after the irradiation light emitted from the light emitting unit 66 is emitted on the component measurement chip 2. The light receiving unit 72 may be configured to measure a light amount of the irradiation light from the light emitting unit 66 in a state where the component measurement chip 2 is not mounted.

Figure 6:
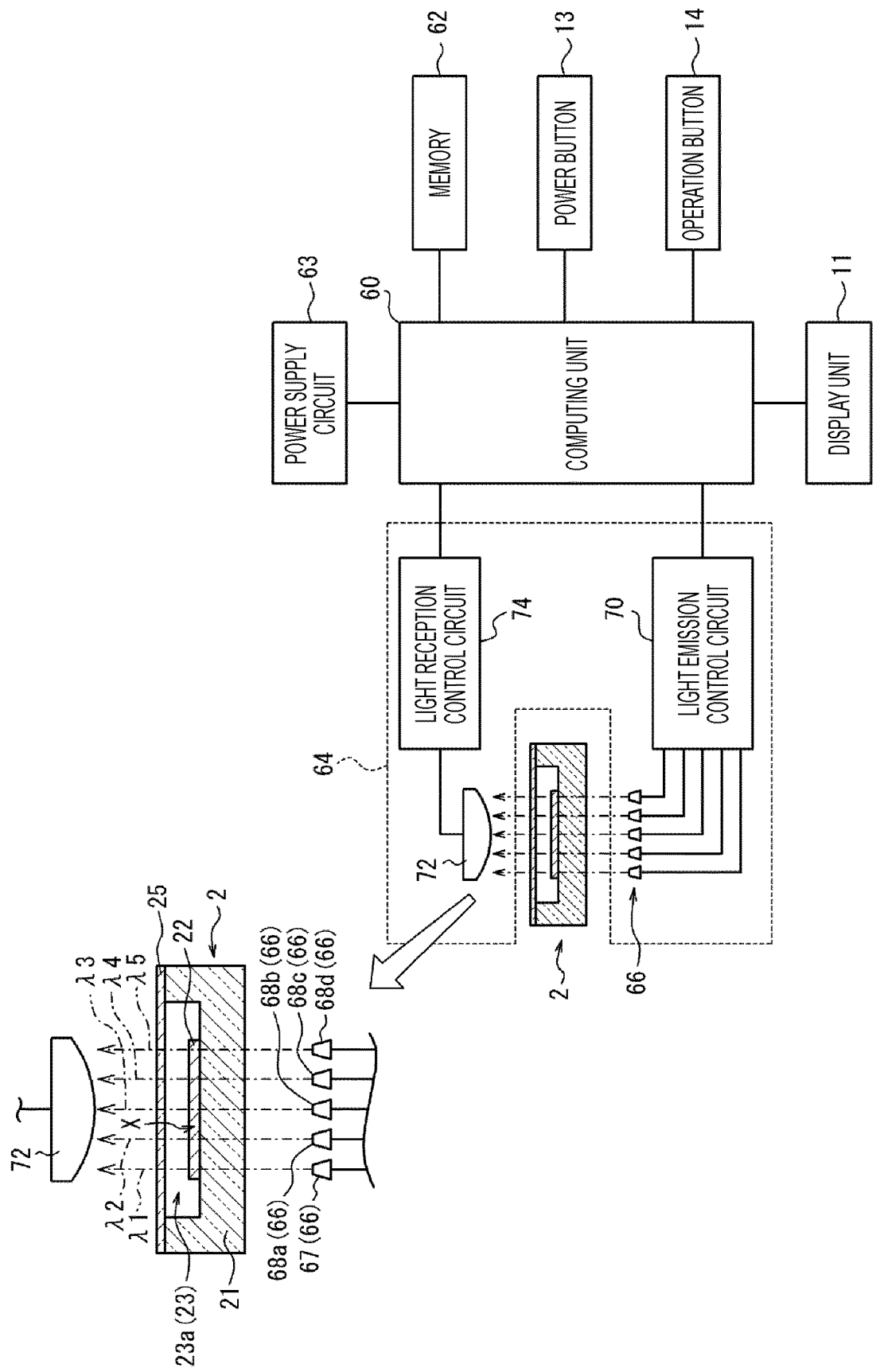
FIG. 6 is an electric block diagram of the component measurement device illustrated in FIG. 1.

As illustrated in FIGS. 2, 3, and 6, the light emitting unit 66 includes five light sources. More specifically, the light emitting unit 66 includes a first light source 67, a second light source 68a, a third light source 68b, a fourth light source 68c, and a fifth light source 68d. In this embodiment, as illustrated in FIG. 3, the first light source 67, the second light source 68a, and the third light source 68b are positioned at different positions along a flow path width direction B (the horizontal direction in FIG. 3) perpendicular to a flow direction A (the rightward direction in FIG. 2) in which the blood flows in a later-described flow path 23 in the component measurement chip 2. Details of the positions of the first light source 67 to the fifth light source 68d will be described later (see FIG. 8).

Figure 4:
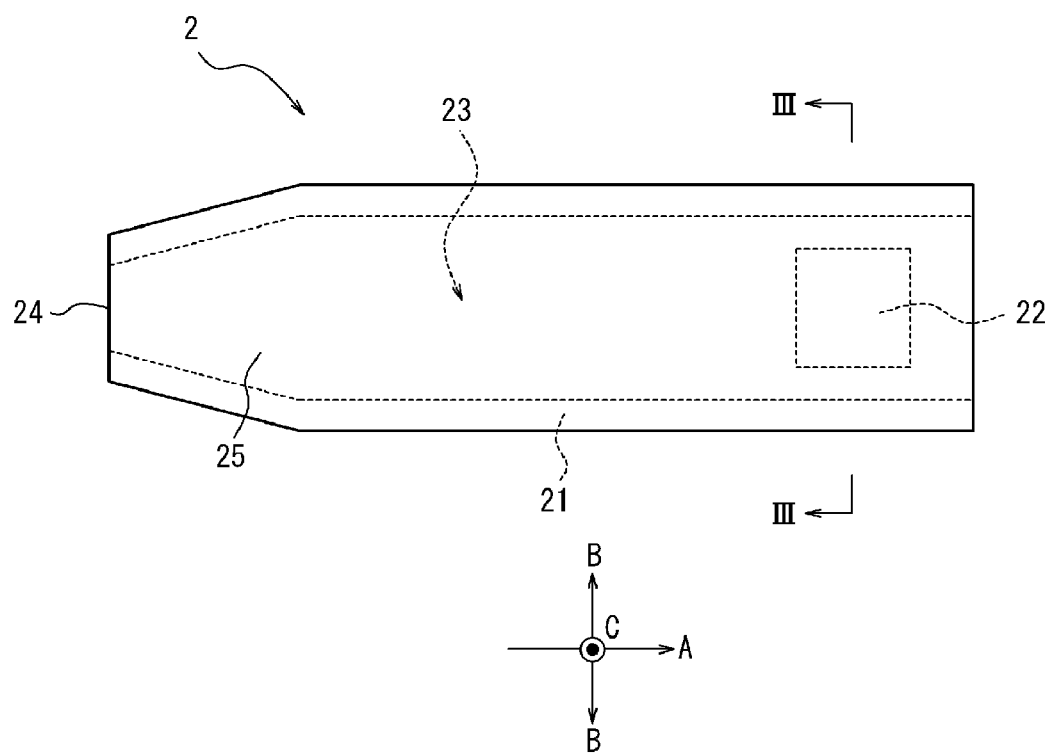
FIG. 4 is a top view of the component measurement chip illustrated in FIG. 1.
Figure 5:
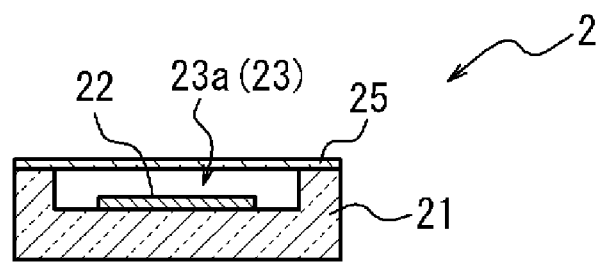
FIG. 5 is a view illustrating a cross section along III-III in FIG. 4.

Next, the component measurement chip 2 will be described. FIG. 4 is a top view of the component measurement chip 2. FIG. 5 is a cross sectional view along III-III in FIG. 4. In the illustration in FIGS. 4 and 5, the component measurement chip 2 is provided with a base member 21 having a substantially rectangular-plate-like outline, a measuring reagent 22 held in the base member 21, and a cover member 25 for covering the base member 21.

The base member 21 has a groove on an outer surface thereof, the outer surface being one side in a thickness direction of the base member 21 (in this embodiment, this direction is equal to the thickness direction C of the component measurement chip 2 illustrated in FIGS. 2 and 3, and therefore, this direction will be referred to as the thickness direction C hereinafter). The groove of the base member 21 is covered with the cover member 25, thereby forming a hollow portion extending in a direction perpendicular to the thickness direction C, and the hollow portion constitutes the flow path 23 of the component measurement chip 2. At one end of the flow path 23, a supplying section 24 capable of supplying blood from outside is provided. Furthermore, the measuring reagent 22 is held in a groove bottom portion of the groove of the base member 21 within inner walls of the flow path 23, and the blood supplied to the supplying section 24 from the outside flows in the flow direction A along the flow path 23 for example by capillary action, reaches a holding position where the measuring reagent 22 is held, and contacts the measuring reagent 22 therein. The measuring reagent 22 contains a coloring reagent that produces a color by a color reaction with blood. Therefore, when the measuring reagent 22 contacts blood, the color reaction takes place to cause the coloring reagent contained in the measuring reagent 22 to produce the color, thereby producing a mixture X (see FIG. 2 and the like) containing a color component.

Furthermore, a space 23a is formed between the cover member 25 and the measuring reagent 22, and the blood moving in the flow direction A through the flow path 23 from the supplying section 24 goes through the space 23a to the other end of the flow path 23. Thus, throughout a whole area of the measuring reagent 22 along the flow direction A, the blood contacts the measuring reagent 22, thereby causing the color reaction. This attains such a state that the mixture X is spread in the whole area of the flow path 23.

In FIG. 2, the holding position of the measuring reagent 22 is labeled as "mixture X" for the sake of easy explanation. However, the mixture X is present not only at the holding position of the measuring reagent 22 but also in a vicinity of the holding position of the measuring reagent 22 such as in the space 23a. More specifically, the blood that has entered the flow path 23 from the supplying section 24 flows via the space 23a, while contacting the measuring reagent 22 at the holding position, and reaches a downstream end of the flow path 23, thereby causing such a state that the flow path 23 is filled with the blood. After that, the color reaction between the measuring reagent 22 and the blood further proceeds, thereby causing such a state that the mixture X is present at the holding position and in the vicinity of the holding position.

Although the flow path 23 of this embodiment includes the hollow portion defined by the base member 21 and the cover member 25, the flow path is not limited to this configuration. A flow path may be formed simply by a groove formed on the external surface of the base member 21, the external surface being one side of the base member 21 in the thickness direction C.

It is preferable that a material(s) of the base member 21 and the cover member 25 be transparent, so that a transmitted light amount after the irradiation light is transmitted therethrough will be enough to be a signal sufficient for measurement. Examples of the transparent materials include transparent organic resin materials such as polyethylene terephthalate (PET), polymethyl methacrylate (PMMA), polystyrene (PS), cyclic polyolefin (COP), cyclic olefin copolymer (COC), and polycarbonate (PC); and transparent inorganic materials such as glass and quartz.

The measuring reagent 22 contains the color reagent that causes color reaction for producing the color according to concentration of a component of interest in blood by reacting with the component of interest in blood. The measuring reagent 22 in this embodiment is applied on the groove bottom portion of the groove serving as the flow path 23. The measuring reagent 22 reacts with glucose in blood, the glucose being the component of interest to measure. Examples of the measuring reagent 22 in this embodiment include (i) glucose oxidase (GOD), (ii) peroxidase (POD), (iii) 1-(4-sulfopheny)-2,3-dimethyl-4-amino-5-pyrazolone, (iv) a mixed reagent of N-ethyl-N-(2-hydroxy-3-sulfopropyl)-3,5-dimethylaniline, sodium salt, and monohydrate (MAOS), or a mixed reagent of glucose dehydrogenase (GDH), tetrazolium salt, and electron mediator, and the like. The measuring reagent 22 may further contain a buffer such as phosphate buffer solution. The kinds and components of the measuring reagent 22 are not limited to these.

However, for the measuring reagent 22 of the present embodiment, a coloring reagent that allows a peak wavelength of absorbance spectrum of the color component produced by the color reaction with glucose in blood to be different from a peak wavelength caused by light absorption characteristics of hemoglobin in hemocyte is selected. The coloring reagent contained in the measuring reagent 22 of the present embodiment is such that the absorbance spectrum of the color component has a peak wavelength around 650 nm, but the coloring reagent contained in the measuring reagent 22 is not limited to such a coloring reagent. The details of this will be described later.

As illustrated in FIG. 2, for measuring a component of interest by the component measurement device 1, the component measurement chip 2 is mounted in the chip attaching portion 10b. When blood is supplied to the supplying section 24 provided at one end of the component measurement chip 2, the blood flows through the flow path 23 for example by capillary action, and reaches the holding position where the measuring reagent 22 is held in the flow path 23. At the holding position, glucose in the blood and the measuring reagent 22 react with each other. As a result, at the holding position in the flow path 23, the mixture X containing the color component is produced. A component measurement device 1 of colorimetric type is configured to irradiate the mixture X containing the color component with irradiation light, and detect a transmitted light amount (or reflected light amount) of the irradiation light, thereby obtaining a detection signal correlated to strength of color production that varies according to the concentration in blood. The component measurement device 1 can measure the component of interest by referring to a calibration curve prepared in advance. The component measurement device 1 according to this embodiment is capable of measuring glucose concentration in the plasma component in blood, as described above.

FIG. 6 is an electric block diagram of the component measurement device 1 illustrated in FIGS. 1 to 3. For convenience, FIG. 6 also illustrates a cross section (the same cross section as illustrated in FIG. 5) of the component measurement chip 2 as attached to the component measurement device 1. FIG. 6 separately illustrates, on the upper left thereof, an enlarged view of the vicinity of the component measurement chip 2. In the following, the component measurement device 1 will be described in more detail.

As illustrated in FIG. 6, in addition to the housing 10, the display unit 11, the detachment lever 12, the power button 13, and the operation button 14, the component measurement device 1 includes a computing unit 60, a memory 62, a power supply circuit 63, and a measurement optical system 64.

The computing unit 60 includes a micro-processing unit (MPU) or a central processing unit (CPU). By reading out and executing a program stored in the memory 62 or the like, the computing unit 60 can realize a control action of each unit. The memory 62 includes a volatile or non-volatile non-transitory storage medium and is configured such that various data (including a program(s)) necessary for carrying out the component measurement method described herein can be read out from and written in the memory 62. In accordance with operations of the power button 13, the power supply circuit 63 supplies power to each unit in the component measurement device 1 including the computing unit 60 or stops supplying the power.

The measurement optical system 64 is an optical system capable of obtaining the optical characteristics of the mixture X containing the color component produced by the color reaction between the glucose in blood and the coloring reagent contained in the measuring reagent 22. More specifically, the measurement optical system 64 includes the light emitting unit 66, a light emission control circuit 70, the light receiving unit 72, and a light reception control circuit 74.

The light emitting unit 66 includes a plurality of light sources. More specifically, the light emitting unit 66 in this embodiment includes five light sources for emitting different kinds of irradiation light (for example, visible light, and infrared light) having different spectral radiant characteristics. More specifically, the light emitting unit 66 includes a first light source 67, a second light source 68a, a third light source 68b, a fourth light source 68c, and the fifth light source 68d. FIG. 6 illustrates a configuration in which the first light source 67 to the fifth light source 68d are in a positional relationship such that these five light sources are aligned in one line for the sake of easy explanation, but the actual positional relationship of the first light source 67 to the fifth light source 68d is different. The actual positional relationship of the first light source 67 to the fifth light source 68d is the one illustrated in FIGS. 2 and 3. Details of the actual positional relationship of the first light source 67 to the fifth light source 68d will be described later (see FIG. 8).

Peak wavelengths of light beams emitted from the first light source 67 to the fifth light source 68d are wavelengths $\lambda 1$ to $\lambda 5$, respectively. As the first light source 67 to the fifth light source 68d, various light emitting elements are applicable such as light emitting diode (LED) elements, organic electro-luminescence (EL) elements, inorganic EL elements, laser diode (LD) elements, and the like. As the first light source 67 to the fifth light source 68d, the LED elements are more easily applicable for the sake of general versatility and the like. In the following explanation, the "peak wavelengths" will be regarded as wavelengths of the light beams emitted from these light sources, respectively, and for the sake of easy explanation, the peak wavelength $\lambda 1$ of the first light source 67 is referred to as "the first predetermined wavelength $\lambda 1$", the peak wavelength $\lambda 2$ of the second light source 68a is referred to as "the second predetermined wavelength $\lambda 2$", the peak wavelength $\lambda 3$ of the third light source 68b is referred to as "the third predetermined wavelength $\lambda 3$", the peak wavelength $\lambda 4$ of the fourth light source 68c is referred to as "the fourth predetermined wavelength $\lambda 4$", and the peak wavelength $\lambda 5$ of the fifth light source 68d is referred to as "the fifth predetermined wavelength $\lambda 5$".

As illustrated in FIGS. 2 and 6, the light receiving unit 72 of this embodiment includes one light receiving element facing the light emitting unit 66 in such a way that the component measurement chip 2 will be between the light receiving unit 72 and the light emitting unit 66. The light receiving unit 72 is configured to receive light that has been transmitted through the component measurement chip 2 after being emitted from the first light source 67 to the fifth light source 68d of the light emitting unit 66, to the mixture X produced on the position where the measuring reagent 22 is held in the component measurement chip 2. Usable examples of the light receiving unit 72 include various types of photoelectric conversion elements such as a photo diode (PD), a photo conductor, and a photo transistor.

The light emission control circuit 70 is configured to supply drive power signals to the first light source 67 to the fifth light source 68d so as to turn on or off the first light source 67 to the fifth light source 68d, respectively. The light reception control circuit 74 is configured to obtain digital signals (hereinafter referred to as "detection signals") by performing logarithmic conversion and A/D conversion of analog signals output from the light receiving unit 72.

Figure 7:
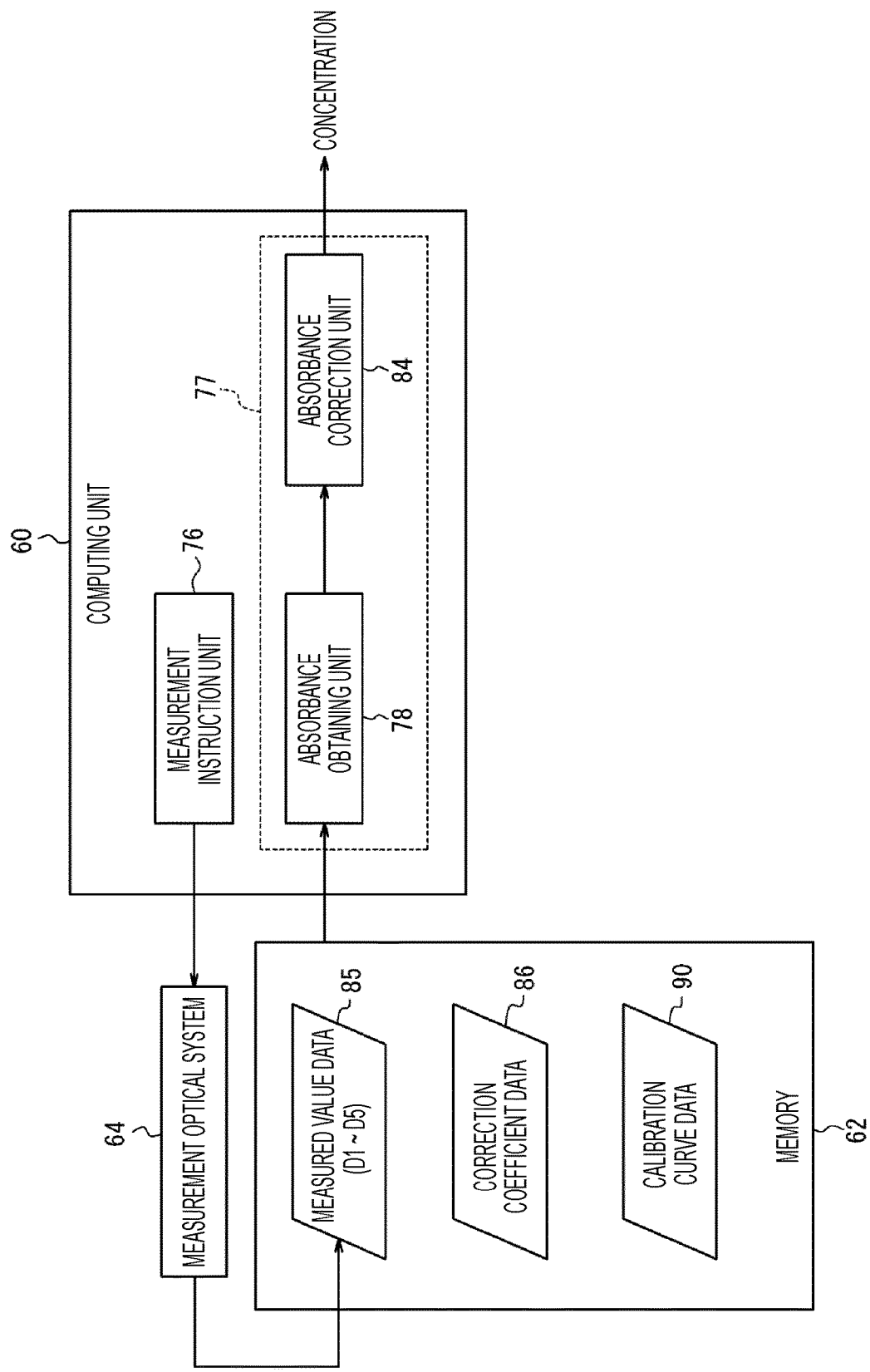
FIG. 7 is a functional block diagram of a computing unit illustrated in FIG. 6.

FIG. 7 is a functional block diagram of the computing unit 60 illustrated in FIG. 6. The computing unit 60 realizes functions of a measurement instruction unit 76 and a concentration measurement unit 77. The measurement instruction unit 76 is configured to give an instruction on measuring operations of the measurement optical system 64, and the concentration measurement unit 77 is configured to work out a concentration of the component of interest by using various data.

The concentration measurement unit 77 includes an absorbance obtaining unit 78 and an absorbance correction unit 84.

In FIG. 7, the memory 62 stores therein: measured value data 85 including the first measured value D1 to the fifth measured value D5, which are absorbance of the mixture X measured by measurement optical system 64 at the first predetermined wavelength $\lambda 1$ to the fifth predetermined wavelength $\lambda 5$, respectively; correction coefficient data 86 including a set of correction coefficients correlated to absorbance of the mixture X at the second predetermined wavelength $\lambda 2$ to the fifth predetermined wavelength $\lambda 5$, respectively; calibration curves representing relationships between various physical amounts (such as glucose concentration) and post-correction absorbance of the color component in the mixture X obtained by correcting, on the basis of the correction coefficient data 86, the absorbance of the mixture X measured at the first predetermined wavelength $\lambda 1$; and calibration curve data 90 such as calibration curves representing a relationship between absorbance of hemoglobin in the mixture X and hematocrit levels. The "hematocrit levels" are values indicated by percentage volume ratios of hemocyte in blood with respect to the blood (whole blood).

As described in detail later, the component measurement device 1 is capable of measuring the component of interest in blood on the basis of the optical characteristics of the mixture X containing the color component generated by the color reaction between the component of interest in the blood and the reagent. More specifically, the component measurement device 1 is capable of estimating a noise amount contained in the first measured value D1 of the absorbance of the mixture X measured by irradiating the mixture X with the irradiation light of the first predetermined wavelength $\lambda 1$ as the measuring wavelength, but not derived from the color component, the component measurement device 1 estimating the noise amount by using the irradiation light of the second predetermined wavelength $\lambda 2$ to the fifth predetermined wavelength $\lambda 5$. More specifically, the component measurement device 1 is capable of estimating the noise amount by using the second measured value D2 to the fifth measured value D5 of the absorbance of the mixture X, which are measured by irradiating the mixture X with the irradiation light of the second predetermined wavelength $\lambda 2$ to the fifth predetermined wavelength $\lambda 5$, and thereby the component measurement device 1 is capable of determining the absorbance of the color component and further the amount of the component of interest.

FIG. 8 is a view illustrating positional relationships of the first light source 67, the second light source 68a, the third light source 68b, the fourth light source 68c, and the fifth light source 68d, where the first light source 67 is configured to emit the irradiation light of the first predetermined wavelength $\lambda 1$ to be emitted to the mixture X, the second light source 68a is configured to emit the irradiation light of the second predetermined wavelength $\lambda 2$ to be emitted to the mixture X, the third light source 68b is configured to emit the irradiation light of the third predetermined wavelength $\lambda 3$ to be emitted to the mixture X, the fourth light source 68c is configured to emit the irradiation light of the fourth predetermined wavelength $\lambda 4$ to be emitted to the mixture X, and the fifth light source 68d is configured to emit the irradiation light of the fifth predetermined wavelength $\lambda 5$ to be emitted to the mixture X. FIG. 8 illustrates the positional relationships of the first light source 67 to the fifth light source 68d when viewed from above the top surface of the component measurement device 1 (see FIG. 1). Furthermore, FIG. 8 illustrates the position of the light receiving unit 72 in the flow path 23 of the component measurement chip 2 by two-dot chain line for the sake of easy explanation. In this embodiment, the mixture X is generated at the holding position and the vicinity thereof in the flow path 23.

As illustrated in FIGS. 2, 3, and 8, the first light source 67 to the fifth light source 68d are so positioned to face the mixture X positioned in the flow path 23 for the blood. More specifically, the first light source 67 to the fifth light source 68d of this embodiment are so positioned to face the holding position of the measuring reagent 22 in the flow path 23 for the blood in the direction (in this embodiment, the direction equal to the thickness direction C of the component measurement chip 2) perpendicular to both of the flow direction A and flow path width direction B.

Furthermore, as illustrated in FIGS. 3 and 8, the first light source 67 and the second light source 68a are positioned in such a way that they are aligned along the flow path width direction B perpendicular to the flow direction A of the blood at the position where the mixture X is present in the flow path 23 for the blood. With this configuration, it becomes easier to set a later-described first irradiation position SL1 (see FIG. 9) and a later-described second irradiation position SL2 (see FIG. 9) at such positions that they at least partially overlap with each other in the flow path width direction B, where the first irradiation position SL1 is that position of the mixture X that is irradiated with the irradiation light from the first light source 67, and the second irradiation position SL2 is that position of the mixture X that is irradiated with the irradiation light from the second light source 68a.

Figure 9:
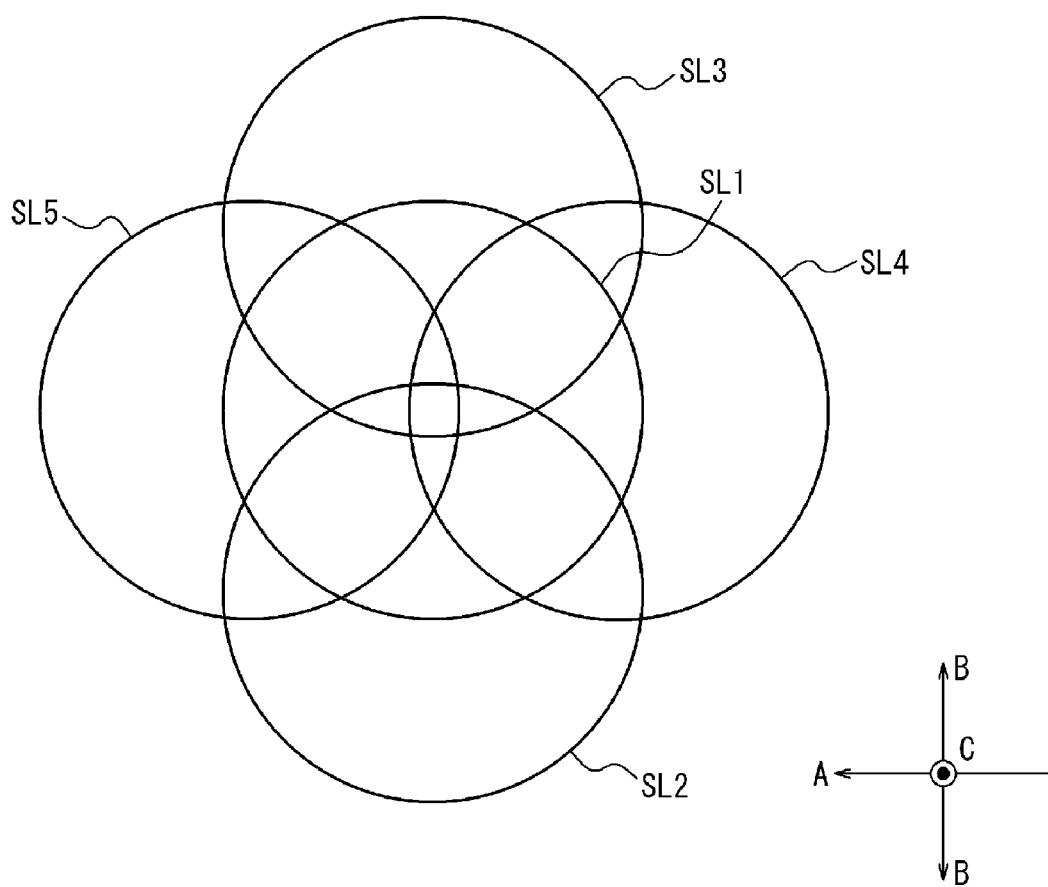
FIG. 9 is a view illustrating radiating positions of a mixture that is irradiated by the plurality of light sources illustrated in FIG. 8.

FIG. 9 is a view illustrating the first irradiation position SL1 to a fifth irradiation position SL5 on the mixture X when viewed from above the top surface of the component measurement device 1 (see FIG. 1), where the first irradiation position SL1 to the fifth irradiation position SL5 are irradiated by the first light source 67 to the fifth light source 68d, respectively. As illustrated in FIG. 9, this embodiment is so configured that the first irradiation position SL1 and the second irradiation position SL2 overlap with each other in the flow path width direction B, where the first irradiation position SL1 is that position of the mixture X that is irradiated with the irradiation light from the first light source 67, and the second irradiation position SL2 is that position of the mixture X that is irradiated with the irradiation light from the second light source 68a. With this configuration, even if the color reaction between the reagent and the blood takes place not-uniformly over the flow direction A due to the influence of the flow of the blood in the flow path 23, it is possible to reduce measurement result fluctuations caused by the non-uniform color reaction. The above described non-uniform reaction is caused due to a gradient of the hemocyte amount over the flow direction A. The gradient of the hemocyte amount over the flow direction A would possibly occur due to dissolution of the measuring reagent 22 that occurs when the color reaction takes place when the blood supplied from one end of the flow path 23 flows in the flow direction A and contacts the measuring reagent 22. When the dissolution of the measuring reagent 22 occurs, the mixture X is generated in such a manner that mainly the plasma component among the components of the blood is taken into the measuring reagent 22. As a result, a ratio of the hemocyte component is increased around the mixture X. The blood as such further flows in the flow direction A. Thus, in the space 23a, the hemocyte amount is greater on the downstream side of the flow direction A than on the upstream side thereof. That is, the gradient of the hemocyte amount occurs in the space 23a. The gradient of the hemocyte amount would possibly cause the non-uniform reaction. Such a gradient of the hemocyte amount is unlikely to occur in the flow path width direction B.

As illustrated in FIG. 9, this embodiment is such that the whole areas of the first irradiation position SL1 and the second irradiation position SL2 in the flow direction A overlap with each other in the flow path width direction B. That is, in this embodiment, the areas of the first irradiation position SL1 and the second irradiation position SL2 are substantially equally positioned along the flow direction A. However, the first irradiation position SL1 and the second irradiation position SL2 are not limited to this positional relationship, but may have any positional relationship, provided that at least part of their areas along the flow direction A overlap with each other in the flow path width direction B. In other words, what is at least required is that part of the area of the first irradiation position SL1 and part of the second irradiation position SL2 are at the same position along the flow direction A. However, with the configuration in which, as in this embodiment, the areas of both of the irradiation positions along the flow direction A overlap wholly with each other in the flow path width direction B, it is possible to further reduce the fluctuations of the measurement result caused by the non-uniform reaction, compared with the configuration in which only parts of the areas along the flow direction A overlap with each other in the flow path width direction B.

Furthermore, the present embodiment is such that the area of the first irradiation position SL1 in the flow path width direction B and the area of the second irradiation position SL2 in the flow path width direction B partially overlap with each other in the flow direction A. In the other words, part of the area of first irradiation position SL1 is at the same position as part of the area of the second irradiation position SL2 in the flow path width direction B. With this configuration, the first irradiation position SL1 and the second irradiation position SL2 can be matched more exactly, thereby making it possible to reduce the fluctuations of the measurement results, which occur depending of measurement positions on the mixture X. It is more preferable that the whole area of the first irradiation position SL1 in the flow path width direction B and the whole area of the second irradiation position SL2 in the flow path width direction B overlap with each other in the flow direction A, that is, that the first irradiation position SL1 and the second irradiation position SL2 be substantially equally positioned in the flow path width direction B.

Furthermore, this embodiment is so configured that, as illustrated in FIGS. 3 and 8, the first light source 67, the second light source 68a, and the third light source 68b are aligned in the flow path width direction B with the first light source 67 positioned in the middle of these light sources. With such a configuration, it also becomes easy to position not only the two areas of the first irradiation position SL1 of the first light source 67 and the second irradiation position SL2 of the second light source 68a in the flow direction A, but also the two areas of the first irradiation position SL1 and the third irradiation position SL3 of the third light source 68b in the flow direction A in a way such that the two areas in the flow direction A at least partly overlap with each other in the flow path width direction B.

As illustrated in FIG. 9, this embodiment is configured such that the area of the first irradiation position SL1 on the mixture X in the flow direction A and the area of the third irradiation position SL3 on the mixture X in the flow direction A overlap with each other in the flow path width direction B, where the first irradiation position SL1 is of the irradiation light from the first light source 67 and the third irradiation position SL3 is of the irradiation light from the third light source 68b. Similarly to the relationship between the first irradiation position SL1 and the second irradiation position SL2, even if the color reaction between the reagent and the blood takes place non-uniformly depending on the position of the reagent in the flow direction A due to the influence of the flow of the blood in the flow path 23, this configuration makes it possible to reduce the fluctuations of the measurement results caused by the non-uniform reaction.

As illustrated in FIG. 9, this embodiment is such that the whole areas of the first irradiation position SL1 and the third irradiation position SL3 in the flow direction A overlap with each other in the flow path width direction B. That is, in this embodiment, the first irradiation position SL1 and the third irradiation position SL3 are substantially equally positioned along the flow direction A. However, the first irradiation position SL1 and the third irradiation position SL3 are not limited to this positional relationship, but may have any positional relationship, provided that at least part of their areas along the flow direction A overlap with each other in the flow path width direction B. In other words, what is at least required is that part of the area of the first irradiation position SL1 and part of the area of the third irradiation position SL3 are at the same position along the flow direction A. However, with the configuration in which, as in this embodiment, the areas of both of the irradiation positions along the flow direction A overlap wholly with each other in the flow path width direction B, it is possible to further reduce the fluctuations of the measurement result caused by the non-uniform reaction, compared with the configuration in which only parts of the areas along the flow direction A overlap with each other in the flow path width direction B.

Furthermore, the present embodiment is such that the area of the first irradiation position SL1 in the flow path width direction B and the area of the third irradiation position SL3 in the flow path width direction B partially overlap with each other in the flow direction A. In the other words, part of the area of first irradiation position SL1 is at the same position as part of the area of the third irradiation position SL3 in the flow path width direction B. With this configuration, the first irradiation position SL1 and the third irradiation position SL3 can be matched more exactly, thereby making it possible to reduce the fluctuations of the measurement results, which occur depending of measurement positions on the mixture X. It is more preferable that the whole area of the first irradiation position SL1 in the flow path width direction B and the whole area of the third irradiation position SL3 in the flow path width direction B overlap with each other in the flow direction A, that is, that the first irradiation position SL1 and the third irradiation position SL3 be substantially equally positioned in the flow path width direction B.

As illustrated in FIG. 9, this embodiment is configured such that the area of the second irradiation position SL2 in the flow direction A and the area of the third irradiation position SL3 in the flow direction A overlap with each other in the flow path width direction B. While the whole areas of the second irradiation position SL2 and the third irradiation position SL3 in the flow direction A of this embodiment overlap with each other in the flow path width direction B, it is only necessary that the areas in the flow direction A at least partly overlap with each other in the flow path width direction B. In other words, what is at least required is that part of the area of the second irradiation position SL2 and part of the area of the third irradiation position SL3 are at the same position along the flow direction A. However, with the configuration in which, as in this embodiment, the areas of both of the irradiation positions along the flow direction A overlap wholly with each other in the flow path width direction B, it is possible to further reduce the fluctuations of the measurement result caused by the non-uniform reaction, compared with the configuration in which only parts of the areas along the flow direction A overlap with each other in the flow path width direction B.

Furthermore, the present embodiment is such that the area of the second irradiation position SL2 in the flow path width direction B and the area of the third irradiation position SL3 in the flow path width direction B partially overlap with each other in the flow direction A. In the other words, part of the area of second irradiation position SL2 is at the same position as part of the area of the third irradiation position SL3 in the flow path width direction B. With this configuration, the second irradiation position SL2 and the third irradiation position SL3 can be matched more exactly, thereby making it possible to reduce the fluctuations of the measurement results, which occur depending of measurement positions on the mixture X. It is more preferable that the whole area of the second irradiation position SL2 in the flow path width direction B and the whole area of the third irradiation position SL3 in the flow path width direction B overlap with each other in the flow direction A, that is, that the second irradiation position SL2 and the third irradiation position SL3 be substantially equally positioned in the flow path width direction B.

As described above, it is preferable that the first light source 67 to the third light source 68b be aligned in the flow path width direction B and the areas of the first irradiation position SL1 to the third irradiation position SL3 in the flow direction A overlap with each other in the flow path width direction B, and it is more preferable that the areas of the first irradiation position SL1 to the third irradiation position SL3 in the flow path width direction B also overlap with each other in the flow direction A.

In this embodiment, the first light source 67 and the second light source 68a are positioned adjacently in the flow path width direction B, and there is no space for providing another light source between the first light source 67 and the second light source 68a. Furthermore, the first light source 67 and the third light source 68b are positioned adjacently in the flow path width direction B, and there is no space for providing another light source between the first light source 67 and the third light source 68b. As such, the first light source 67, the second light source 68a, and the third light source 68b are positioned adjacently in the flow path width direction B without another light source provided therebetween. Thus, it is easy to realize such a configuration that the areas of the first irradiation position SL1, the second irradiation position SL2, and the third irradiation position SL3 overlap with each other in the flow direction A.

Next, positional relationships between the first light source 67, and the fourth light source 68c and the fifth light source 68d will be described. As illustrated in FIGS. 2 and 8, the first light source 67 and the fourth light source 68c of this embodiment are aligned in the flow direction A. Furthermore, as illustrated in FIGS. 2 and 8, the first light source 67 and the fifth light source 68d of this embodiment are aligned in the flow direction A. More specifically, the first light source 67, the fourth light source 68c, and the fifth light source 68d are aligned in the flow direction A with the first light source 67 positioned in the middle of these light sources.

As described above, the second light source 68a and the third light source 68b are positioned adjacently with the first light source 67 in the flow path width direction B. In order to reduce the fluctuations of the measurement results due to the flow of blood in the flow path 23, it is preferable that the fourth light source 68c and the fifth light source 68d be aligned with the first light source 67 in the flow path width direction B. However, in the case of the configuration where the fourth light source 68c and the fifth light source 68d are aligned with the first light source 67 in the flow path width direction B, it is not possible to position the first light source 67 adjacently with each of the fourth light source 68c and the fifth light source 68d respectively due to the presence of the second light source 68a and the third light source 68b. Therefore, the first light source 67 is more distanced from each of the fourth light source 68c and the fifth light source 68d in the flow path width direction B than the first light source 67 is distanced from each of the second light source 68a and the third light source 68b in the flow path width direction B. When the distance is larger, it would possibly become more difficult to attain a configuration in which the area of the first irradiation position SL1 of the first light source 67 in the flow path width direction B overlaps with each of the areas of the fourth irradiation position SL4 of the fourth light source 68c and the fifth irradiation position SL5 of the fifth light source 68d in the flow path width direction B in the flow direction A. That is, it would likely become a configuration in which the area of the first irradiation position SL1 does not overlap with each of the areas of the fourth irradiation position SL4 and the fifth irradiation position SL5 at all. If the area first irradiation position SL1 did not overlap with each of the areas of the fourth irradiation position SL4 and the fifth irradiation position SL5, the absorbance would be measured at different locations, thereby deteriorating the measurement results of the component of interest to measure. It is also possible to cause the area of the first irradiation position SL1 of the first light source 67 to overlap with each of the areas of the fourth irradiation position SL4 of the fourth light source 68c and the fifth irradiation position SL5 of the fifth light source 68d by tilting the fourth light source 68c and the fifth light source 68d. However, in this case, the differences between an incident angle of the irradiation light from the first light source 67 to the mixture X and an incident angle of the irradiation light from each of the fourth light source 68c and the fifth light source 68d to the mixture X becomes too large. The large difference in incident angle would result in a large difference between a light path length of the irradiation light from the first light source 67 to the mixture X and a light path length of the irradiation light from each of the fourth light source 68c and the fifth light source 68d to the mixture X. Furthermore, this would result in the difference between an interface reflection of the irradiation light from the first light source 67 and an interface reflection of the irradiation light from each of the fourth light source 68c and the fifth light source 68d. The differences in light path length and interface reflection influence the measured values of the absorbance. That is, such a case would possibly result in deterioration of estimation accuracy of the noise amount in the measured values of absorbance measured by using the irradiation light from the first light source 67.

Therefore, this embodiment is configured such that the first light source 67 and the fourth light source 68c are aligned in the flow direction A in such a way that the areas of the first irradiation position SL1 and the fourth irradiation position SL4 overlap with each other with the differences in incident angles to the mixture X being equal to or less than a predetermined value. More specifically, it is so configured that there is no space for providing another light source between the first light source 67 and the fourth light source 68c in the flow direction A, and the first light source 67 and the fourth light source 68c are adjacent to each other in the flow direction A. Compared with a configuration in which the first light source 67 and the fourth light source 68c are aligned in the flow path width direction B, this configuration is more susceptible to the influence of the flow of blood, but is capable of further improving the estimation accuracy of the noise amount by overlapping their irradiation positions with a smaller difference in incident angle.

Therefore, this embodiment is configured such that the first light source 67 and the fifth light source 68d are also aligned in the flow direction A in such a way that the areas of the first irradiation position SL1 and the fifth irradiation position SL5 overlap with each other with the differences in incident angles to the mixture X being equal to or less than a predetermined value. More specifically, there is no space for providing another light source between the first light source 67 and the fifth light source 68d in the flow direction A, and the first light source 67 and the fifth light source 68d are adjacent to each other in the flow direction A.

Furthermore, the first light source 67 is adjacent to each of the second light source 68a and the third light source 68b in the flow path width direction B, thereby making it possible to overlap the first irradiation position SL1 with each the second irradiation position SL2 and the third irradiation position SL3 with the differences in incident angle to the mixture X being equal to or less than a predetermined value. That is, the second light source 68a and the third light source 68b of this embodiment have such a relationship with the first light source 67 that the second light source 68a and the third light source 68b are not so susceptible to the influence of the flow of blood, and the areas of the second light source 68a and the third light source 68b overlap with each other with a smaller difference in incident angle between the first light source 67 and each of the second light source 68a and the third light source 68b.

This embodiment is so configured that the second light source 68a and the third light source 68b are aligned with the first light source 67 in the flow path width direction B, where the second light source 68a and the third light source 68b emit the irradiation light of the second predetermined wavelength λ2 and the third predetermined wavelength λ3, which are relatively large in degree of influence to the estimation of the noise amount contained in the measured value of the absorbance measured by using the irradiation light of the first predetermined wavelength λ1 from the first light source 67. Furthermore, this embodiment is configured such that the fourth light source 68c and the fifth light source 68d are aligned with the first light source 67 in the flow direction A, where the fourth light source 68c and the fifth light source 68d emit the fourth predetermined wavelength λ4 and the fifth predetermined wavelength λ5, which are relatively small in degree of influence to the estimation of the noise amount contained in the measured value of the absorbance measured by using the irradiation light of the first predetermined wavelength λ1 from the first light source 67, compared with the second predetermined wavelength λ2 and the third predetermined wavelength λ3. With this configuration, it is possible to improve the estimate accuracy of the noise amount. Details of "degree of influence" to the estimation of noise amount will be described below (see FIG. 14). In the aforementioned configuration, the second predetermined wavelength λ2 and the third predetermined wavelength λ3 are wavelengths belonging to the infrared region, whereas the fourth predetermined wavelength λ4 and the fifth predetermined wavelength λ5 are wavelengths belonging to the visible region, as described later in detail.

Moreover, as illustrated in FIGS. 2 and 3, the light receiving unit 72 is so positioned to face the first light source 67 to the fifth light source 68d in the thickness direction C in such a way that the mixture X is between the light receiving unit 72 and the first light source 67 to the fifth light source 68d when the mixture X is positioned in the flow path 23 of the component measurement chip 2 attached. As described above, the light receiving unit 72 positioned as such is configured to receive the transmitted light that is that portion of the irradiation light from the first light source 67 to the fifth light source 68d that has been transmitted through the mixture X. As illustrated in FIGS. 2 and 3, the component measurement device 1 includes a first diaphragm unit 69a positioned to be between the mixture X and the light receiving unit 72, and configured to control how much of the transmitted light that has been transmitted through the mixture X reaches the light receiving unit 72. As described above, the estimation accuracy of the noise amount is influenced by the difference between the incident angle of the irradiation light from the first light source 67 to the mixture X and the incident angle of the irradiation light from each of the second light source 68a to the fifth light source 68d to the mixture X. Therefore, it is preferable that the difference between the incident angle of the irradiation light from the first light source 67 to the mixture X and the incident angle of the irradiation light from each of the second light source 68a to the fifth light source 68d to the mixture X be small. That is, it is preferable that distances T1 in a facing direction be long for the sake of a better estimation accuracy of the noise amount, where the facing direction is equal to the thickness direction C of component measurement chip 2 in FIGS. 2 and 3, and the distances T1 are the distances between the first diaphragm unit 69a and the first light source 67 to the fifth light source 68d. Further, with a configuration in which distances T2 in the facing direction are short, where the distances T2 are distances between the light receiving unit 72 and the first light source 67 to the fifth light source 68d, it is possible to improve light efficiency and downsize the component measurement device 1.

Furthermore, if the area of the first irradiation position SL1 of the first light source 67 and each of the areas of the second irradiation positions SL2 to the fifth irradiation position SL5 of the second light source 68a to the fifth light source 68d are positioned with a large difference (hereinafter, this difference is referred to as "measurement field difference"), the measurement positions would not be so uniform, whereby the accuracy of the measurement results of the component of interest would be possibly deteriorated. Therefore, it is preferable that the measurement field difference be small. Thus, it is preferable that a distance T3 in the facing direction be short, where the distance T3 is a distance between the mixture X and the first diaphragm unit 69a, and the facing direction is equal to the thickness direction C of the component measurement chip 2 in FIGS. 2 and 3.

Furthermore, as illustrated in FIGS. 2 and 3, the component measurement device 1 includes a second diaphragm unit 69b positioned to be between the mixture X and the first light source 67 to the fifth light source 68d, and configured to control how much light reaches the mixture X from the first light source 67 to the fifth light source 68d. Especially, it is preferable that the second diaphragm unit 69b be designed in such a way that, among the light emitted from the first light source 67 to the fifth light source 68d, light reflected on an inner wall of the second diaphragm unit 69b (hereinafter, this light is referred to as "stray light") will not enter the first diaphragm unit 69a. It is possible to assume that the light emitted from the first light source 67 to the fifth light source 68d is optically attenuated to 5% by reflection on a wall once, and disappears after 3 or more multiple reflections. Therefore, if this embodiment was configured such that the stray light reflected on the inner wall of the second diaphragm unit 69b does not reach the first diaphragm unit 69a but is reflected on another wall, the multiple reflection would prevent the stray light from entering the first diaphragm unit 69a. In the present embodiment, it is designed that optical axes of the light sources will be reflected on the inner wall of the second diaphragm unit 69b by specular reflection. However, in reality, diffuse reflection occurs on the inner wall of the second diaphragm unit 69b, thereby giving a certain distribution of the stray light. Therefore, it is preferable in this embodiment that the aforementioned distance T4 and the like be set such that, even if part of the stray light enters the first diaphragm unit 69a, the part of the stray light will enter the first diaphragm unit 69a at an incident angle different from the incident angle of the first light source 67 by a predetermined value or less.

By adjusting the positions and the like of the first diaphragm unit 69a and the second diaphragm unit 69b as described above, the differences in incident angles of the irradiation light and the measurement field differences are kept within the predetermined ranges. Incidentally, the optical system of the component measurement device 1 does not include a lens such as a collecting lens. The use of a lens would make it possible to improve light collecting efficiency by positioning the lens near a light source, but it requires to maintain the positional relationship between the light source and the lens precisely, thereby requiring high assembly accuracy, or requires an additional step for adjusting fluctuations in the positional relationship between the light source and the lens. Therefore, in the component measurement device 1, a configuration with high measurement accuracy is realized, without using a lens, setting the positions and the like of the first diaphragm unit 69a and the second diaphragm unit 69b, without requiring high assembly accuracy.

As described above, in the component measurement device 1, the reduction in the influence of the flow of blood in the flow direction A in the flow path 23 of the blood and the improvement in the estimation accuracy of the noise amount are realized by positioning the first light source 67 to the fifth light source 68d at the predetermined positions.

The component measurement device 1 according to the present embodiment is such that the flow path 23 for the flow of blood is defined and the component measurement chip 2 is mountable in the flow path 23, the component measurement chip 2 being provided with the measuring reagent 22 containing the coloring reagent that causes the color reaction with the component of interest in the blood. When the component measurement chip 2 is mounted thereto, the component measurement device 1 according to the present embodiment can measure the component of interest in the blood on the basis of the optical characteristics of the mixture including the color component produced in the flow path 23 by the reaction with the component of interest. Furthermore, the component measurement device 1 is provided with the first light source 67 and the second light source 68a to the fifth light source 68d for emitting irradiation light of the second predetermined wavelength λ2 to the fifth predetermined wavelength λ5. The first light source 67 is configured to emit the irradiation light of the first predetermined wavelength λ1 to be emitted to the mixture X in the flow path 23 of the component measurement chip 2 attached to the component measurement device 1. The second light source 68a to the fifth light source 68d are configured to emit the irradiation light of the second predetermined wavelength λ2 to the fifth predetermined wavelength λ5 to be emitted to the mixture X in the flow path 23 of the component measurement chip 2 attached to the component measurement device 1, so as to be used for the estimation of the noise amount in the measured value of the absorbance of the mixture X measured by the light amount of the transmitted portion of the irradiation light of the first light source 67, the noise amount being caused by disturbance factor and derived other than from the color component. Furthermore, the first light source 67 to the third light source 68b are aligned along the flow path width direction B perpendicular to the flow direction A of the blood and positioned for the mixture X present in the flow path 23 of the component measurement chip 2 attached to the component measurement device 1.

As described above, the component measurement device 1 according to the present embodiment is capable of measuring the absorbance of the mixture X in the attachable/detachable component measurement chip 2, but may be so configured that the attachable/detachable feature of the component measurement chip 2 is not required. However, for the sake of user friendliness, environmental issues, and the like, it is preferable that the component measurement device 1 be reusable and the component measurement chip 2 be disposable and attachable to/detachable from the component measurement device 1.

As illustrated in FIG. 8, the first light source 67 to the fifth light source 68d are held by a holder member 80 having a thin-plate like shape. The holder member 80 of this embodiment has a cross-like outline when viewed from the top. The first light source 67 is positioned at a center portion (a crossing portion of the cross) when viewed from the top. The second light source 68a is held on one extension portion in the flow path width direction B from the center portion where the first light source 67 is held, and the third light source 68b is held on the other extension portion in the flow path width direction B. Furthermore, the fifth light source 68d is held on one extension in the flow direction A from the center portion where the first light source 67 is held, and the fourth light source 68c is held on the other extension portion in the flow direction A.

In the following, described is a component measurement method including: causing the color reaction between glucose as the component of interest in blood and the coloring reagent in the measuring reagent 22 by reacting the coloring reagent with the blood (whole blood) without separating from the blood a plasma component containing glucose; estimating absorbance of a color component at a predetermined measuring wavelength on the basis of absorbance of a mixture X at various wavelengths, the mixture X being produced by the color reaction, and the color component being generated by the color reaction between glucose and the coloring reagent; and calculating out concentration of the component of interest in the blood.

To begin with, referring to FIGS. 10 and 11, drawbacks in estimating the component of interest in blood on the basis of absorbance measurement of blood (whole blood) will be described. In the following Examples, a measuring reagent 22 is used that contains, as the coloring reagent, a tetrazolium salt (WST-4), and glucose dehydrogenase (GDH) and an electron mediator mixed therein.

Figure 10:
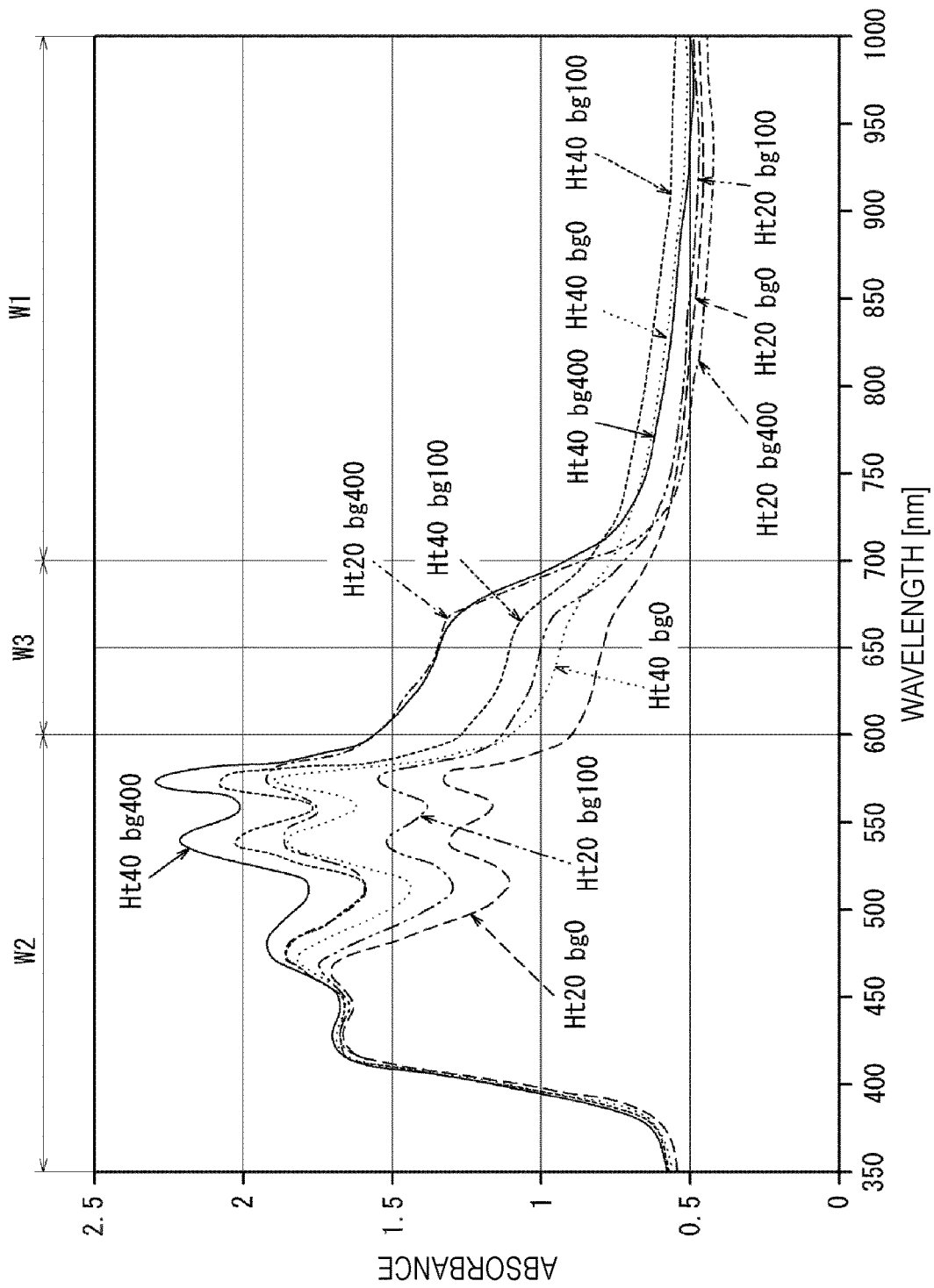
FIG. 10 is a graph illustrating absorbance spectra of six kinds of mixtures each obtained by a color reaction between a respective one of six kinds of blood samples and a measuring reagent.

FIG. 10 illustrates absorbance spectra of six kinds of mixtures X each of which is obtained by a reaction between a respective one of six kinds of blood samples and the measuring reagent 22. A hematocrit level and a glucose concentration of each blood sample are known. These six kinds of blood samples are referred to as first to sixth samples. The first sample has a hematocrit level of 20% and a glucose concentration of 0 mg/dL (denoted as "Ht20 bg0" in FIG. 10). The second sample has a hematocrit level of 20% and a glucose concentration of 100 mg/dL (denoted as "Ht20 bg100" in FIG. 10). The third sample has a hematocrit level of 20% and a glucose concentration of 400 mg/dL (denoted as "Ht20 bg400" in FIG. 10). The fourth sample has a hematocrit level of 40% and a glucose concentration of 0 mg/dL (denoted as "Ht40 bg0" in FIG. 10). The fifth sample has a hematocrit level of 40% and a glucose concentration of 100 mg/dL (denoted as "Ht40 bg100" in FIG. 10). The sixth sample has a hematocrit level of 40% and a glucose concentration of 400 mg/dL (denoted as "Ht40 bg400" in FIG. 10).

Figure 11:
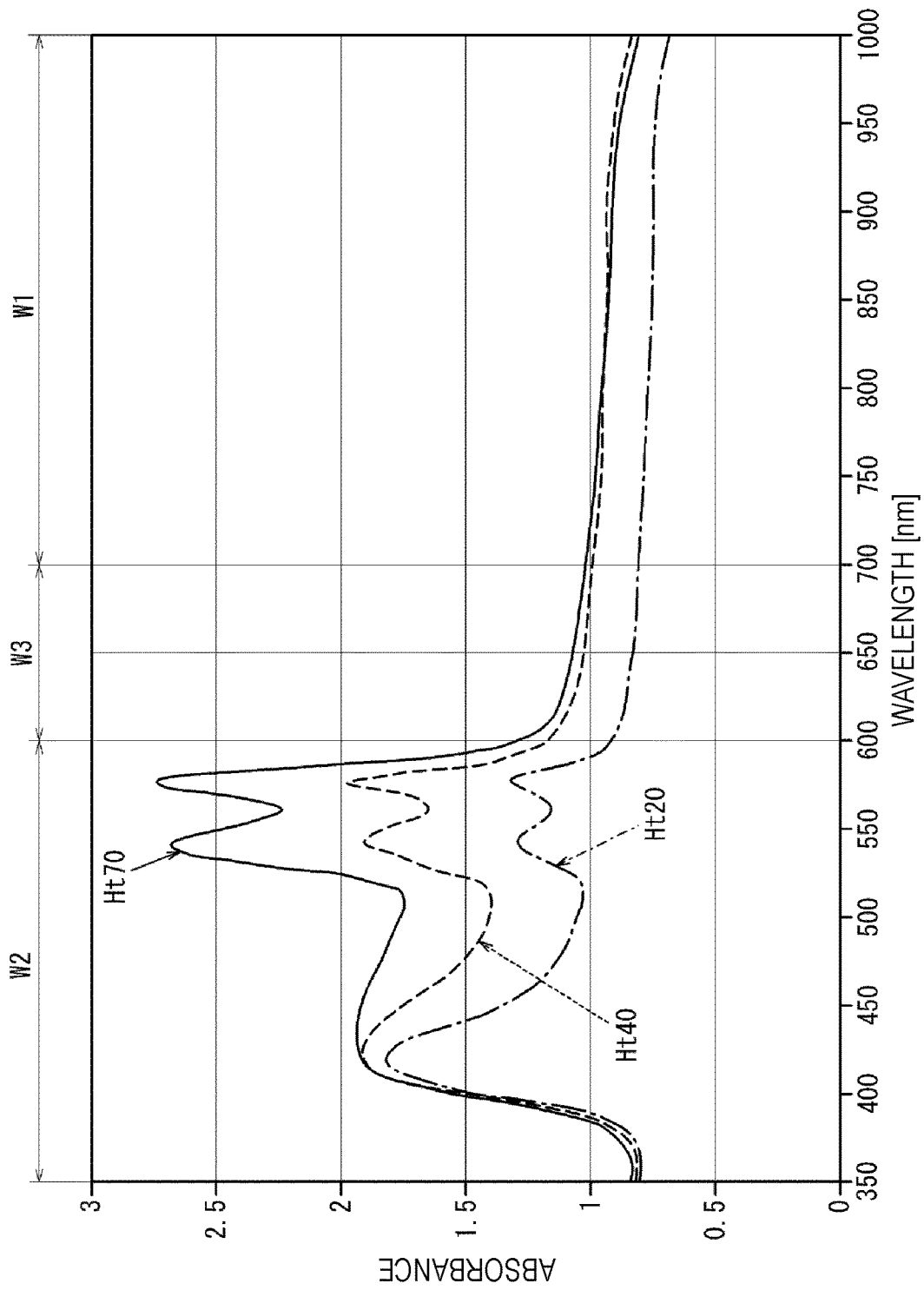
FIG. 11 is a graph illustrating absorbance spectra of seven kinds of blood samples.

FIG. 11 illustrates absorbance spectra of seven kinds of blood samples whose hematocrit level and glucose concentration are known. These seven kinds of blood samples are referred to as first to seventh samples. The first to sixth samples are the same as the first to sixth samples illustrated in FIG. 10. The seventh sample has a hematocrit level of 70% and a glucose concentration of 100 mg/dL. These blood samples with an equal hematocrit level have substantially equivalent absorbance spectra, and therefore FIG. 11 illustrates only three curves for different hematocrit levels. Specifically, three curves illustrated in FIG. 11 represent the samples having the hematocrit level of 20% (denoted as "Ht20" in FIG. 11), 40% (denoted as "Ht40" in FIG. 11), and 70% (denoted as "Ht70" in FIG. 11).

In general, when a sample contains a component other than the color component whose absorbance is to be measured, the component other than the color component would possibly cause optical phenomenon and thereby act as a disturbance factor (noise) that influences the measurement results of the concentration of the component of interest measured on the basis of the absorbance of the color component. For example, measurements tend to result in a larger absorbance than a true value when "light scattering" due to a hemocyte component in blood, the surface of the component measurement chip or particulates such as dusts adhered on the component measurement chip, or "light absorption" due to a pigmentary component (specifically, hemoglobin) other than the color component of interest occurs.

Specifically, the absorbance spectra of the blood samples illustrated in FIG. 11 mainly have two peaks centered around 540 nm and around 570 nm. These two peaks are chiefly caused by light absorption of oxygenated hemoglobin in erythrocytes. In the absorbance spectra of the blood samples illustrated in FIG. 11, in a wavelength band of 600 nm or more, each absorbance gradually decreases in a substantially straight line as the wavelength becomes longer. The substantially straight line is chiefly caused by light scattering caused by the hemocyte component, the particulates such as dusts adhered to the component measurement chip, and the like.

In other words, the light scattering due to the hemocyte component and the like dominantly influences the absorbance of each blood sample in the wavelength band longer than the wavelength around 600 nm. In regard to the wavelength band shorter than the wavelength around 600 nm, the light absorption due to the hemoglobin dominantly influences the absorbance of each blood sample rather than the light scattering due to the hemocyte component and the like.

On the other hand, the absorbance spectra of the mixtures X illustrated in FIG. 10 are such that, similarly to the absorbance spectra of the blood illustrated in FIG. 11, each shows a trend curve with the absorbance gradually decreasing as the wavelength becomes longer. However, as compared with the curves illustrated in FIG. 11, the absorbance spectra of the mixtures X illustrated in FIG. 10 show high absorbance around a wavelength band of visible light, about 600 nm to 700 nm. The increase in absorbance around the range of 600 nm to 700 nm is mainly due to the absorption characteristics of the color component produced by the color reaction between glucose in the blood and the coloring reagent in the measuring reagent 22.

As seen above, in order to accurately measure the absorbance derived from the color component by using not only the color component of interest but also the mixture X containing blood having the light absorption characteristics illustrated in FIG. 11, it is required to remove the disturbance factor (noise) such as the light scattering due to the hemocyte component and the like, and the light absorption due to the hemoglobin from a measured value of absorbance at a predetermined measuring wavelength (for example, 650 nm).

More specifically, it is necessary to estimate how much the disturbance factor (noise) such as the light scattering due to the hemocyte component and the like, and the light absorption due to the hemoglobin is caused at a predetermined measuring wavelength (for example, 650 nm) at which absorptivity of the pigmentary component of interest to be measured is high, and to correct a measured value of absorbance at the measuring wavelength accordingly.

Hereinafter, a component measurement method carried out by the component measurement device 1 will be described in detail.

The component measurement device 1 can measure the component of interest in the blood based on the optical properties of the mixture X containing the color component generated by the color reaction between the blood and the measuring reagent 22. Specifically, in this embodiment, a glucose concentration in the plasma component in the blood is measured.

Furthermore, the component measurement device 1 can calculate out a glucose concentration in the blood by correcting the measured value of the absorbance of the mixture X measured at the measuring wavelength by correcting the measured value on the basis of the optical properties due to the hemocyte component in the blood, the surface of the component measurement chip 2, or the particulates such as dust adhered to the component measurement chip 2 and based on a ratio between the reduced hemoglobin and the oxygenated hemoglobin in erythrocytes. In other words, the component measurement method carried out by the component measurement device 1 involves a step of correcting the measured value of the absorbance of the mixture X measured at the measuring wavelength by correcting the measured value based on information of the scattered light due to the hemocyte component in the blood, the surface of the component measurement chip 2, or the particulates such as dust adhered to the component measurement chip 2, and based on the ratio between the reduced hemoglobin and the oxygenated hemoglobin in erythrocytes.

Figure 12:
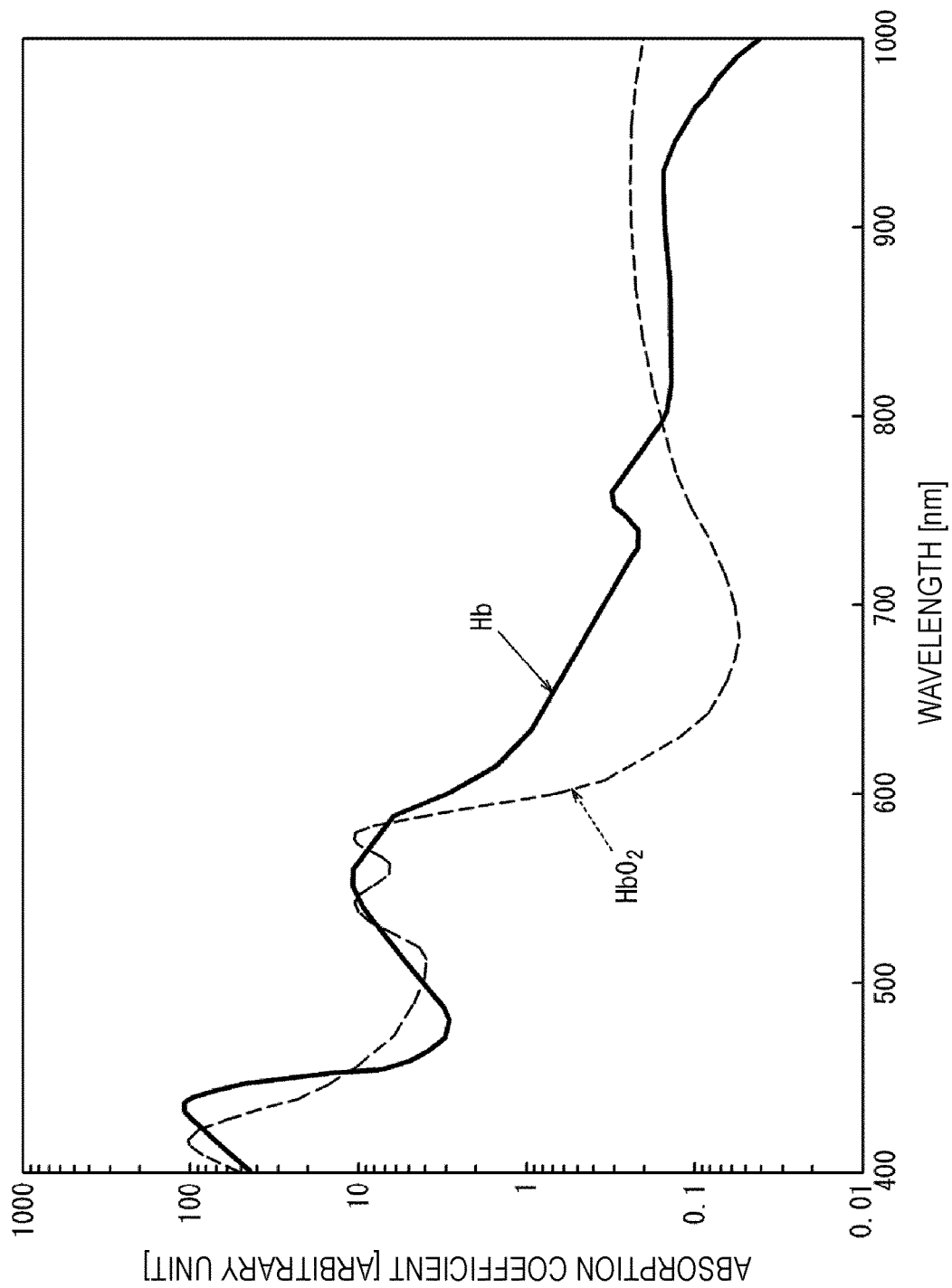
FIG. 12 is a graph illustrating an absorption coefficient of reduced hemoglobin and an absorption coefficient of oxygenated hemoglobin.

FIG. 12 illustrates an absorption coefficient of the reduced hemoglobin (denoted as "Hb" in FIG. 12) and an absorption coefficient of the oxygenated hemoglobin (denoted as "HbO2" in FIG. 12). Hemoglobin in erythrocytes mainly includes oxygenated hemoglobin combined with oxygen, and reduced hemoglobin from which oxygen has been dissociated when the hemoglobin was in a place where oxygen partial pressure was low. Reduced hemoglobin passes through lungs and combines with oxygen, thereby becoming oxygenated hemoglobin that plays the role of transporting oxygen throughout the body through arteries and is mainly abundant in arterial blood. For example, when collecting blood from a finger pad, the collected blood is from a capillary so that the blood contains a relatively large amount of oxygenated hemoglobin. Conversely, reduced hemoglobin is mainly abundant in venous blood.

Figure 13:
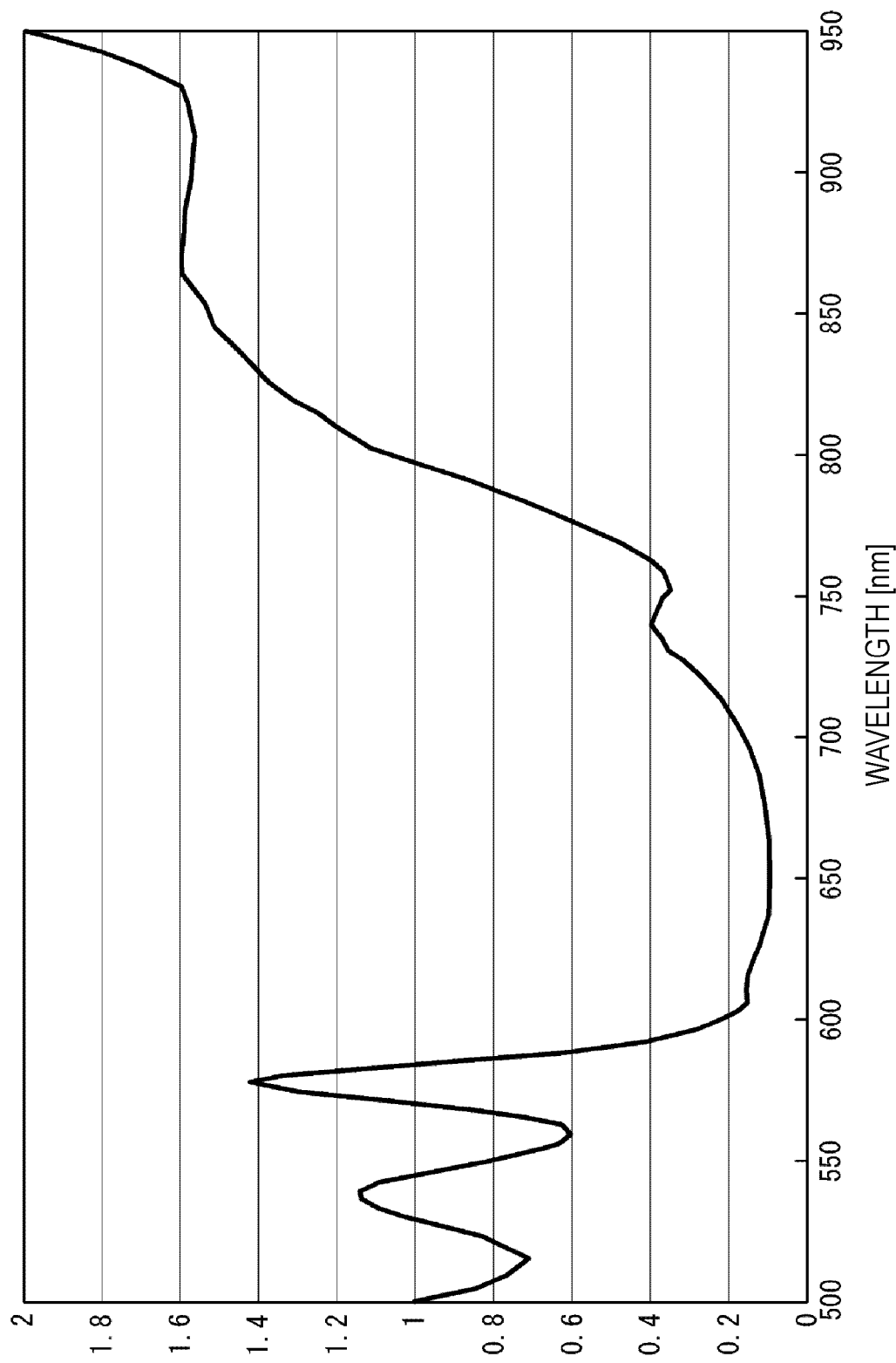
FIG. 13 is a graph illustrating a ratio of the absorption coefficient of the oxygenated hemoglobin to the absorption coefficient of the reduced hemoglobin.

In a typical existing technique, the absorbance corresponding to the color component of interest measured at the measuring wavelength is corrected by using, for example, a hematocrit level, without considering the ratio between the reduced hemoglobin and the oxygenated hemoglobin. However, as demonstrated in FIG. 12, the absorption coefficient of the reduced hemoglobin is not equal to the absorption coefficient of the oxygenated hemoglobin, and therefore an amount of absorbance of the reduced hemoglobin and an amount of absorbance of the oxygenated hemoglobin differ depending on wavelengths. FIG. 13 is a graph illustrating a ratio of the absorption coefficient of the oxygenated hemoglobin to the absorption coefficient of the reduced hemoglobin. For example, when the measuring wavelength for measuring the absorbance of the color component of interest is 650 nm, the absorption coefficient of the reduced hemoglobin is about 0.9, and the absorption coefficient of the oxygenated hemoglobin is about 0.09. In other words, the absorption coefficient of the oxygenated hemoglobin is equivalent to about 10% of the absorption coefficient of the total hemoglobin. In order to estimate the absorbance derived from the color component of interest more accurately, it is important to consider the ratio between the reduced hemoglobin and the oxygenated hemoglobin.

Therefore, the component measurement device 1 is configured such that the measuring wavelength for measuring the absorbance of the color component contained in the mixture X is set to 650 nm, and the measured value of the absorbance of the mixture X measured at this measuring wavelength is corrected by removing, from the measured value, as disturbance factors (noise), the influence of the light scattering of the hemocyte component and the like and the influence of the light absorption of the hemoglobin, while taking the ratio between the reduced hemoglobin and the oxygenated hemoglobin into account for the influence of the light absorption of the hemoglobin. By doing this the component measurement device 1 estimates the absorbance of the color component contained in the mixture X, and calculates the glucose concentration on the basis of the calibration curve representing the relationship between this estimated absorbance and a glucose concentration.

Hereinafter, the component measurement method carried out by the component measurement device 1 will be described in more detail.

The coloring reagent in the measuring reagent 22 used in this embodiment is such that the absorbance of the color component produced by the color reaction with glucose in blood has a peak around 600 nm, but the measuring wavelength for measuring the absorbance of the color component is set to 650 nm in this embodiment.

The measuring wavelength for measuring the absorbance of the color component of interest may be a wavelength at which absorptivity of the color component is relatively high and the influence of the light absorption of the hemoglobin is relatively small. More specifically, the measuring wavelength may be within a wavelength band W3 that corresponds to the full width at half maximum of a peak wavelength band in the absorbance spectrum of the color component of interest and in which a ratio of absorbance depending on the light absorption of the hemoglobin to the total absorbance is relatively small (see FIGS. 10 and 11). What is meant by a wavelength band that "corresponds to the full width at half maximum in a peak wavelength band" is a range from a wavelength indicating a half width on the short-wavelength side to a wavelength indicating a half width on the long-wavelength side within a wavelength band specified as the full width at half maximum of the peak wavelength band in the absorbance spectrum. In the absorbance spectrum of the color component of interest in this embodiment, the peak wavelength is around 600 nm, and a wavelength band from about 500 nm to about 700 nm corresponds to the full width at half maximum. Furthermore, the influence of the light absorption of the hemoglobin in the total absorbance is relatively small at the wavelength band of 600 nm or more. Therefore, in this embodiment, the range not less than 600 nm but not more than 700 nm is the wavelength band W3 that corresponds to the full width at half maximum of the peak wavelength band in the absorbance spectrum of the color component of interest and in which the ratio of absorbance depending on the light absorption of the hemoglobin to the total absorbance is relatively small. Therefore, the measuring wavelength is not limited to 650 nm as in this embodiment, and another wavelength within the range from 600 nm to 700 nm may be used as the measuring wavelength. For the sake of more accurately measuring the absorbance derived from the color component, it is more advantageous to select a wavelength band where a signal indicating the absorbance of the color component is strong and at which the ratio of absorbance depending on the light absorption of the hemoglobin to the total absorbance is as low as possible. Therefore, it is preferable to set the measuring wavelength to a wavelength around 650 nm, which is slightly longer than the wavelength around 600 nm, which is the peak wavelength of the absorbance spectrum of the color component. More specifically, the measuring wavelength is preferably in a range from 630 nm to 680 nm, more preferably in a range from 640 nm to 670 nm, or particularly preferably 650 nm as in this embodiment. Preferable examples of such a coloring reagent include a tetrazolium salt, and, for example, WST-4 is most preferable.

Furthermore, this embodiment employs the coloring reagent with which the full width at half maximum of the peak wavelength band in the absorbance spectrum of the color component is about 500 nm to about 700 nm, however, this embodiment may employ a coloring reagent having its full width at half maximum of a peak wavelength band within a range different from the above range. However, as described above, in consideration of the light absorption characteristics of the hemoglobin, it is desirable that the measuring wavelength in the absorbance spectrum of the color component do not overlap with the wavelength band where the absorbance depending on the light absorption of the hemoglobin becomes large (600 nm or less).

In the following, a method for estimating the absorbance of the color component at 650 nm, that is the measuring wavelength of this embodiment, will be described. The component measurement device 1 measures the absorbance of the mixture X at four wavelengths different from the measuring wavelength (650 nm), namely the second predetermined wavelength $\lambda 2$ to the fifth predetermined wavelength $\lambda 5$. By using the four measured values, namely the second measured value D2 to the fifth measured value D5 and the predetermined correction coefficient data 86, the component measurement device 1 corrects the first measured value D1 of the absorbance of the mixture X measured at the measuring wavelength so as to estimate the absorbance of the color component at the measuring wavelength. In the present embodiment, the measuring wavelength is the first predetermined wavelength $\lambda 1$ described above.

More specifically, as the four of the second measured value D2 to the fifth measured value D5, the component measurement device 1 uses the second measured value D2 and the third measured value D3 that are two measured values of the absorbance of the mixture X measured at two of the second predetermined wavelength $\lambda 2$ and the third predetermined wavelength $\lambda 3$ longer than the first predetermined wavelength $\lambda 1$ that is the measuring wavelength; and the fourth measured value D4 and the fifth measured value D5 that are two measured values of the absorbance of the mixture X measured at two of the fourth predetermined wavelength $\lambda 4$ and the fifth predetermined wavelength $\lambda 5$ shorter than the first predetermined wavelength $\lambda 1$ that is the measuring wavelength.

More specifically, as the four of the second measured value D2 to the fifth measured value D5, the component measurement device 1 uses the second measured value D2 and the third measured value D3, which are two measured values of the absorbance of the mixture X measured at two of the second predetermined wavelength $\lambda 2$ and the third predetermined wavelength $\lambda 3$, which are two wavelengths within a wavelength band longer than the first predetermined wavelength $\lambda 1$ that is the measuring wavelength, at which the influence of the light scattering of the hemocyte component and the like is dominant in the total absorbance; and the fourth measured value D4 and the fifth measured value D5, which are two measured values of the absorbance of the mixture X measured at the fourth predetermined wavelength $\lambda 4$ and the fifth predetermined wavelength $\lambda 5$, which are two wavelengths within a wavelength band shorter than the first predetermined wavelength $\lambda 1$ that is the measuring wavelength, at which the influence of the light absorption of the hemoglobin is large in the total absorbance.

In other words, as the second measured value D2 and the third measured value D3, the component measurement device 1 uses the absorbance of the mixture X measured at wavelengths that are within a wavelength band longer than the measuring wavelength that is within a wavelength band corresponding to the full width at half maximum of the peak wavelength band in the absorbance spectrum of the color component of interest (500 nm to 700 nm in this embodiment), that is, for example, the component measurement device 1 uses, as the second measured value D2 and the third measured value D3, the absorbance of the mixture X measured at the second predetermined wavelength $\lambda 2$ and the third predetermined wavelength $\lambda 3$ belonging to a long wavelength band W1 longer than the wavelength band W3.

In addition, as the fourth measured value D4 and the fifth measured value D5, the component measurement device 1 uses the fourth measured value D4 and the fifth measured value D5, the absorbance of the mixture X at the fourth predetermined wavelength $\lambda 4$ and the fifth predetermined wavelength $\lambda 5$, which are within a wavelength band shorter than the measuring wavelength, which is within a wavelength band corresponding to the full width at half maximum of the peak wavelength band in the absorbance spectrum of the color component of interest (500 nm to 700 nm), that is, for example, a short wavelength band W2 shorter than the wavelength band W3.

The absorbance obtaining unit 78 of the component measurement device 1 obtains the first measured value D1 to the fifth measured value D5. More specifically, the mixture X is irradiated by the first light source 67 to the fifth light source 68d of the light emitting unit 66 with emitted light beams including emission wavelengths of the first predetermined wavelength $\lambda 1$ to the fifth predetermined wavelength $\lambda 5$, respectively. The light receiving unit 72 receives transmitted light that is that portion of the emitted light beams that have passed through the mixture X. The computing unit 60 calculates out the absorbance of the mixture X at each of these wavelengths from the relationship between the emitted light and the transmitted light and stores, in the memory 62, the absorbance of the mixture X at each of these wavelengths, that is, the first measured value D1 to the fifth measured value D5 as the measured value data 85. The absorbance obtaining unit 78 of the component measurement device 1 can obtain the measured value data 85 from the memory 62. The obtaining of the first measured value D1 to the fifth measured value D5 by the absorbance obtaining unit 78 is not limited to the above, and may be carried out by various known ways.

The absorbance correction unit 84 of the component measurement device 1 corrects the first measured value D1 by using the second measured value D2 to the fifth measured value D5, thereby estimating the absorbance of the color component at the first predetermined wavelength $\lambda 1$ that is the measuring wavelength (650 nm in this example).

Particularly, as seen from FIGS. 10 and 11, the absorbance spectrum of the mixture X is substantially linear at the long wavelength band W1 at which the light scattering of the hemocyte component and the like is dominant. Therefore, as long as the second measured value D2 that is the absorbance at the second predetermined wavelength $\lambda 2$, and the third measured value D3 that is the absorbance at the third predetermined wavelength $\lambda 3$, are obtained, determination of a slope between the second measured value D2 and the third measured value D3 makes it possible to estimate, to some extent, the absorbance derived from the disturbance factor (noise) excluding the absorbance derived from the color component at the first predetermined wavelength $\lambda 1$ that is the measuring wavelength. The component measurement device 1 can calculate a glucose concentration in blood in such a way that, besides the optical properties due to the hemocyte component and the like in the blood, the ratio between the reduced hemoglobin and the oxygenated hemoglobin in erythrocytes is also taken into consideration. Therefore, the component measurement device 1 is capable of performing correction with higher accuracy by using two wavelengths (the fourth predetermined wavelength and the fifth predetermined wavelength) selected in accordance with the ratio between the reduced hemoglobin and the oxygenated hemoglobin.

Specifically, it may be configured such that the fourth predetermined wavelength $\lambda 4$ is a wavelength at which a difference in absorption coefficient between the reduced hemoglobin and the oxygenated hemoglobin is equal to or less than a first predetermined value, and the fifth predetermined wavelength $\lambda 5$ is a wavelength at which the difference in absorption coefficient between the reduced hemoglobin and the oxygenated hemoglobin is larger than the first predetermined value. More specifically, it may be configured such that the fourth predetermined wavelength $\lambda 4$ is a wavelength at which a ratio of the absorption coefficient of the oxygenated hemoglobin to the absorption coefficient of the reduced hemoglobin (see FIG. 13) is equal to or more than a first threshold that is a predetermined threshold, and the fifth predetermined wavelength $\lambda 5$ is a wavelength at which the ratio of the absorption coefficient of the oxygenated hemoglobin to the absorption coefficient of the reduced hemoglobin is less than the first threshold. In other words, as the fourth predetermined wavelength $\lambda 4$ and the fifth predetermined wavelength $\lambda 5$, the following two wavelengths are used: the wavelength at which the ratio of the absorption coefficient of the oxygenated hemoglobin to the absorption coefficient of the reduced hemoglobin is equal to or more than the first threshold; and the wavelength at which the ratio is less than the first threshold. Accordingly, for correcting the first measured value D1 with the second measured value D2 to the fifth measured value D5, the absorbance correction unit 84 is capable of highly accurately performing the correction in consideration of the ratio between the reduced hemoglobin and the oxygenated hemoglobin.

As the two wavelengths selected in accordance with the ratio between the reduced hemoglobin and the oxygenated hemoglobin, it is preferable to use two wavelengths at which a difference in light absorption of the hemoglobin depending on the ratio between the reduced hemoglobin and the oxygenated hemoglobin is large. Therefore, as the fourth predetermined wavelength $\lambda 4$, this embodiment employs a wavelength at which the ratio of the absorption coefficient of the oxygenated hemoglobin to the absorption coefficient of the reduced hemoglobin is 0.8 or more, that is, a wavelength ranging from 520 nm to 550 nm, or from 565 nm to 585 nm. As the fifth predetermined wavelength $\lambda 5$, it is preferable to use a wavelength at which the ratio of the absorption coefficient of the oxygenated hemoglobin to the absorption coefficient of the reduced hemoglobin is less than 0.8, that is, a wavelength more than 550 nm and less than 565 nm, or more than 585 nm and less than 600 nm. However, as the fourth predetermined wavelength $\lambda 4$, it is preferable to use a wavelength at which the absorption coefficient of the reduced hemoglobin and the absorption coefficient of the oxygenated hemoglobin are equal so that it is possible to simultaneously estimate the amount of the whole hemoglobin and the hematocrit level. In other words, in this embodiment, it is preferable to use a wavelength around 530 nm, around 545 nm, around 570 nm, or around 580 nm, and it is particularly preferable to use a wavelength ranging from 540 to 545 nm where the absorption coefficient of the whole hemoglobin is large. Furthermore, as the fifth predetermined wavelength $\lambda 5$, it is preferable to use a wavelength more than 550 nm and less than 565 nm, particularly, around 560 nm where the difference in absorption coefficient is a maximum. Alternatively, it is preferable to use a wavelength more than 585 nm and less than 600 nm, particularly, around 590 nm where the difference in absorption coefficient is a maximum.

As such, as for the short wavelength band W2 where the light absorption of the whole hemoglobin largely varies depending on the ratio between the reduced hemoglobin and the oxygenated hemoglobin, the fourth predetermined wavelength $\lambda 4$ and the fifth predetermined wavelength $\lambda 5$ at which the difference in the light absorption of the whole hemoglobin is large are adopted, thereby making it possible to accurately estimate the absorbance of noise at the first predetermined wavelength $\lambda 1$ or the measuring wavelength (650 nm in this embodiment), in consideration of the ratio between the reduced hemoglobin and the oxygenated hemoglobin. Therefore, with the component measurement device 1, the absorbance of the color component at the first predetermined wavelength $\lambda 1$ or the measuring wavelength, and the component of interest (glucose concentration in this embodiment) can be measured with accuracy.

In this embodiment, only the fourth predetermined wavelength $\lambda 4$ and the fifth predetermined wavelength $\lambda 5$ are set to wavelengths at which the influence of the ratio between the reduced hemoglobin and the oxygenated hemoglobin is taken into account to a large degree. It is more preferable that, in addition to the fourth predetermined wavelength $\lambda 4$ and the fifth predetermined wavelength $\lambda 5$, the second predetermined wavelength $\lambda 2$ and the third predetermined wavelength $\lambda 3$ be such wavelengths.

Specifically, as the second predetermined wavelength $\lambda 2$ within the long wavelength band W1 where the light scattering of the hemocyte component and the like is dominant, a wavelength at which the difference in absorption coefficient between the reduced hemoglobin and the oxygenated hemoglobin is equal to or less than a second predetermined value is used, and as the third predetermined wavelength $\lambda 3$ similarly within the long wavelength band W1, a wavelength band where the difference is larger than the second predetermined value is used. More specifically, as the second predetermined wavelength $\lambda 2$, it is preferable to use a wavelength at which the ratio of the absorption coefficient of the oxygenated hemoglobin to the absorption coefficient of the reduced hemoglobin is equal to or more than the first threshold and equal to or lower than the second threshold, and as the third predetermined wavelength $\lambda 3$ similarly within the long wavelength band W1, it is preferable to use a wavelength at which the ratio of the absorption coefficient of the oxygenated hemoglobin to the absorption coefficient of the reduced hemoglobin is less than the first threshold or more than the second threshold. The second threshold is a predetermined threshold other than and larger than the first threshold. In other words, as the second predetermined wavelength $\lambda 2$ and the third predetermined wavelength $\lambda 3$, it is preferable to use two wavelengths within the range where the ratio of the absorption coefficient of the oxygenated hemoglobin to the absorption coefficient of the reduced hemoglobin is one different from the above. With this configuration, for correcting the first measured value D1 with the second measured value D2 to the fifth measured value D5, the absorbance correction unit 84 is capable of highly accurately performing the correction in which the ratio between the reduced hemoglobin and the oxygenated hemoglobin is taken into account to a greater degree.

Particularly, at the long wavelength band W1, the influence of the light scattering of the hemocyte component and the like is dominant, but the light absorption of the hemoglobin also influences in the extent similar to the measuring wavelength of the component of interest. Therefore, as the second predetermined wavelength $\lambda 2$ and the third predetermined wavelength $\lambda 3$, it is preferable to use two wavelengths at which the light absorption of the hemoglobin varies relatively largely in accordance with the ratio between the reduced hemoglobin and the oxygenated hemoglobin.

Therefore, in this embodiment, it is preferable to use, as the second predetermined wavelength $\lambda 2$, a wavelength within a range where the ratio of the absorption coefficient of the oxygenated hemoglobin to the absorption coefficient of the reduced hemoglobin is not less than 0.8 but not more than 1.5, preferably within a range from 790 nm to 850 nm. However, it is particularly preferable that the second predetermined wavelength $\lambda 2$ is selected from around the wavelengths where the light absorption of the hemoglobin is relatively large at the long wavelength band W1, that is, where the absorption coefficient of the reduced hemoglobin is equal to the absorption coefficient of oxygenated hemoglobin. In this embodiment, it is particularly preferable to use a wavelength selected from the range of 800 nm to 810 nm.

Furthermore, the third predetermined wavelength $\lambda 3$ is set to a wavelength within the long wavelength band W1 where the absorbance of the color component included in the total absorbance at the third predetermined wavelength $\lambda 3$ is 10% or less, preferably 6% or less, more preferably 3% or less, still more preferably substantially 0%, of the absorbance of the color component included in the total absorbance at the measuring wavelength. In other words, it is particularly preferable to use a wavelength equal to or longer than a wavelength that is the bottom of the long-wavelength side of the peak wavelength band in the absorbance spectrum of the color component. This removes the influence of the light absorption of the color component, thereby enabling accurate estimation of the noise in which the influence of the light scattering of the hemocyte component and the like is dominant at the long wavelength band W1. Therefore, in this embodiment, it is more preferable to use a wavelength of not less than 725 nm but less than 790 nm as the third predetermined wavelength λ3. Because it is most preferable that the third predetermined wavelength λ3 be a wavelength closer to the measuring wavelength, it is particularly preferable that the third predetermined wavelength λ3 be a wavelength at which the absorbance of the color component is zero, that is, the bottom of the long-wavelength side of the peak wavelength band in the absorbance spectrum of the color component. Therefore, in this embodiment, it is particularly preferable that the third predetermined wavelength λ3 be 755 nm. The term "total absorbance" used in a phrase "the absorbance of the color component included in the total absorbance" indicates the absorbance of the whole mixture. The expression "the absorbance of the color component" used in the phrase "the absorbance of the color component included in the total absorbance" indicates the absorbance of a reactant generated by the color reaction between the component of interest in the blood and the coloring reagent in the reagent, that is, the absorbance derived from the color component in the mixture.

As described above, the component measurement device 1 performs such correction that the first measured value D1, which is the measured value of the absorbance of the mixture X at the measuring wavelength, is corrected by using the second measured value D2 to the fifth measured value D5, which are the measured values of the absorbance of the mixture X at the second predetermined wavelength λ2 to the fifth predetermined wavelength λ5, thereby making it possible to estimate the absorbance of the color component at the measuring wavelength.

Hereinafter, a correction method carried out by the absorbance correction unit 84 of the component measurement device 1 will be described.

As described above, the memory 62 of the component measurement device 1 stores the measured value data 85 of the first measured value D1 to the fifth measured value D5, which indicates the absorbance of the mixture X at each of the first predetermined wavelength λ1 to the fifth predetermined wavelength λ5 measured by the measurement optical system 64; the correction coefficient data 86, which includes a set of correction coefficients correlated with the absorbance of the mixture X at each of the second predetermined wavelength λ2 to the fifth predetermined wavelength λ5; and the calibration curve data 90, which includes a calibration curve representing a relationship between various physical quantities and the absorbance of the color component in the mixture X obtained by correcting the absorbance of the mixture X actually measured at the first predetermined wavelength λ1 based on the correction coefficient data 86.

Based on the measured value data 85 and the correction coefficient data 86 stored in the memory 62, the absorbance correction unit 84 calculates the absorbance of the color component at the fifth wavelength λ5 that is the measuring wavelength.

The correction coefficient data 86 herein is obtained by regression analysis computed in advance based on the following Formula 1.

$$B(\lambda 1)=b0+b1*B(\lambda 2)+b2*B(\lambda 3)+b3*B(\lambda 4)+b4*B(\lambda 5) \quad \text{[Math. 1]}$$

The symbol B(λ) represents the absorbance derived from the disturbance factor (noise) at a wavelength λ except the absorbance of the color component at the wavelength λ, and the coefficients b0, b1, b2, b3, and b4 are obtained by regression calculation based on the Formula 1 for various kinds of blood samples. Specifically, this embodiment was so configured that based on the selection criteria of the second predetermined wavelength λ2 to the fifth predetermined wavelength λ5, wavelengths of 810 nm, 750 nm, 545 nm, and 560 nm were used as the second predetermined wavelength λ2, the third predetermined wavelength λ3, the fourth predetermined wavelength λ4, and the fifth predetermined wavelength λ5, respectively. The various kinds of blood samples are basically six blood samples having different component compositions. The blood samples were prepared with adjusted hematocrit levels in a range of 10% to 70%. The absorbance spectrum of each adjusted blood sample was measured and subjected to regression analysis so as to obtain the coefficients b0, b1, b2, b3, and b4. This time, the observations was carried out 766 times in total. Based on these coefficients b0 to b4 thus obtained, a set of correction coefficients correlated with the absorbance of the mixture X at respective ones of the second predetermined wavelength λ2 to the fifth predetermined wavelength λ5 was obtained. By using the correction coefficient data 86 including the correction coefficients, the measured value of the absorbance of the mixture X at the measuring wavelength of 650 nm was corrected on the basis of the measured values of the absorbance of the mixture X at 545 nm, 560 nm, 750 nm, and 810 nm, thereby making it possible to estimate the absorbance of the color component at 650 nm.

Here, each of the coefficients b0 to b4 obtained by the regression calculation can be definable as a value specific to that measurement system, but not as a value varying depending on hematocrit levels. Therefore, the numerical values (measured values) of B(λ2) to B(λ5) used in the regression calculation fluctuate depending on hematocrit levels.

Figure 14:
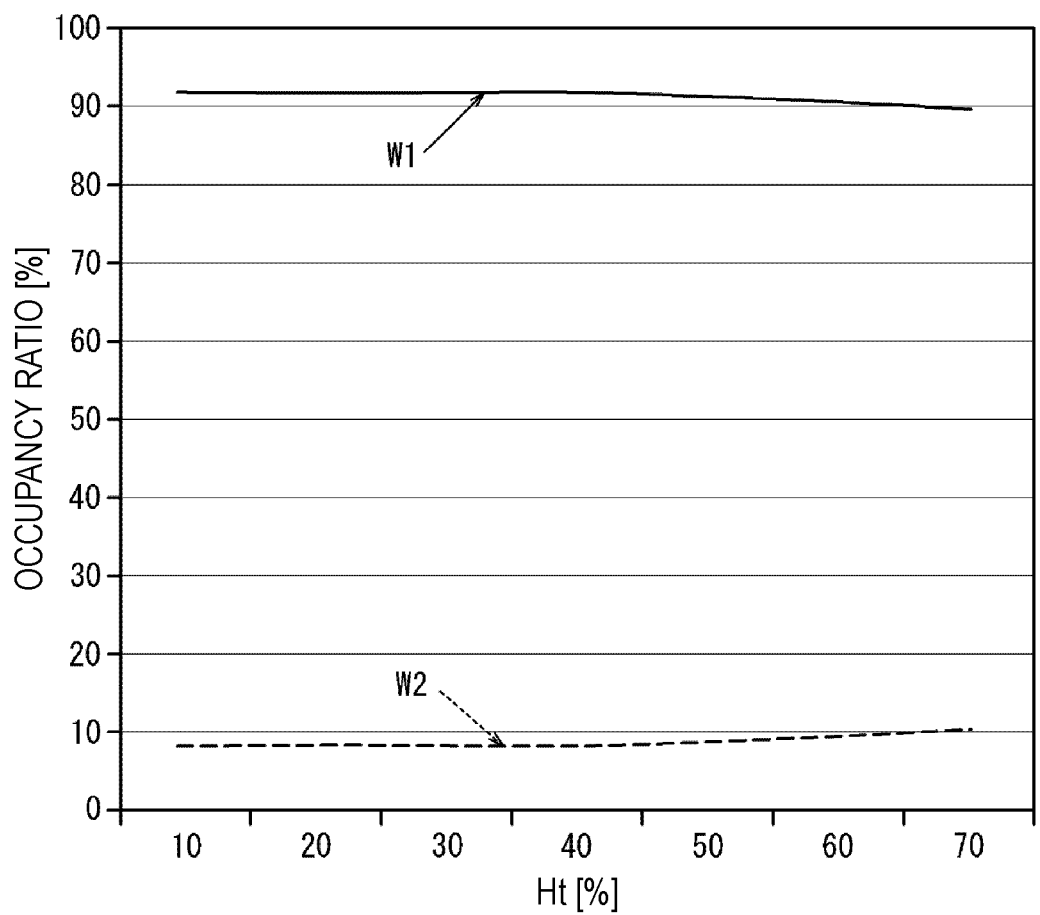
FIG. 14 is a graph illustrating an occupancy ratio of a long wavelength band and that of a short wavelength band within absorbance at a measurement wavelength, the absorbance being estimated by regression analysis as being caused by disturbance factor (noise) other than a color component.

FIG. 14 is a graph illustrating the degree of influence of measured values in the long wavelength band W1 (this degree of influence is indicated as "W1" in FIG. 14) and the degree of influence of measured values in the short wavelength band W2 (this degree of influence is indicated as "W2" in FIG. 14) in the aforementioned regression calculation with respect to the noise amount (hereinafter, it can be simply mentioned as "a noise absorbance") that is the absorbance caused at the measuring wavelength by the disturbance factor (noise) other than the color component. The term "degree of influence" herein means the occupancy ratio in data. As illustrated in FIG. 14, the results of measured data obtained by the regression calculation demonstrates that, when the noise absorbance at the first predetermined wavelength λ1 that was the measuring wavelength was estimated by using the second measured value D2 to the fifth measured value D5, the second measured value D2 and the third measured value D3 respectively at the second predetermined wavelength λ2 and the third predetermined wavelength λ3 in the long wavelength band W1 reduced their degrees of influence from 92% to 90% as the hematocrit level increased from 10% to 70% (see "W1" in FIG. 14). Meanwhile, the fourth measured value D4 and the fifth measured value D5 at the fourth predetermined wavelength λ4 and the fifth predetermined wavelength λ5 in the short wavelength band W2 increased their degrees of influence from 8% to 10% as the hematocrit level increased from 10% to 70% (see "W2" in FIG. 14). These changes in the degrees of influence in the long wavelength band W1 and the short wavelength band W2 used depending on the hematocrit level make it possible to more accurately estimate the noise absorbance occurring at the measured wavelength, thereby consequently making it possible to more accurately estimate the absorbance of the color component at the measuring wavelength. Furthermore, in the case in which the absorbance of the color component is contained in the second measured value D2 to the fifth measured value D5, it is necessary to carry out correction calculation for the second measured value D2 to the fifth measured value D5, in order to calculate out the B ($\lambda$) that is the noise absorbance.

In the component measurement device 1, when the fourth predetermined wavelength $\lambda 4$ is a wavelength at which the absorption coefficient of the reduced hemoglobin is equal to the absorption coefficient of the oxygenated hemoglobin at the short wavelength band W2 where the influence of the light absorption of the hemoglobin is overwhelmingly large (in FIG. 12, 530 nm, 545 nm, 570 nm, or 580 nm), the hematocrit level can be calculated from the fourth measured value D4 or from the fourth measured value D4 and the second measured value D2 obtained by the wavelength at which the absorption coefficient of the reduced hemoglobin is equal to the absorption coefficient of the oxygenated hemoglobin (in FIG. 12, 800 nm) in the long wavelength band W1 where the influence of the light scattering of the hemocyte component and the like is large. The hematocrit level can be calculated from the calibration curve of the absorbance of the hemoglobin against the hematocrit level, the calibration curve being stored in the memory 62.

Described below is results of verification experiments regarding accuracy of the estimation of the absorbance of the color component at the measuring wavelength that was estimated by the component measurement device 1 based on the optical properties including the scattered light caused by the hemocyte component and the like in the blood and dust and the like and based on the ratio between the reduced hemoglobin and the oxygenated hemoglobin in erythrocytes. The samples (n=766) were prepared by adjusting the hematocrit levels of the blood to 10%, 20%, 30%, 40%, 50%, 60%, and 70%.

Figure 15A:
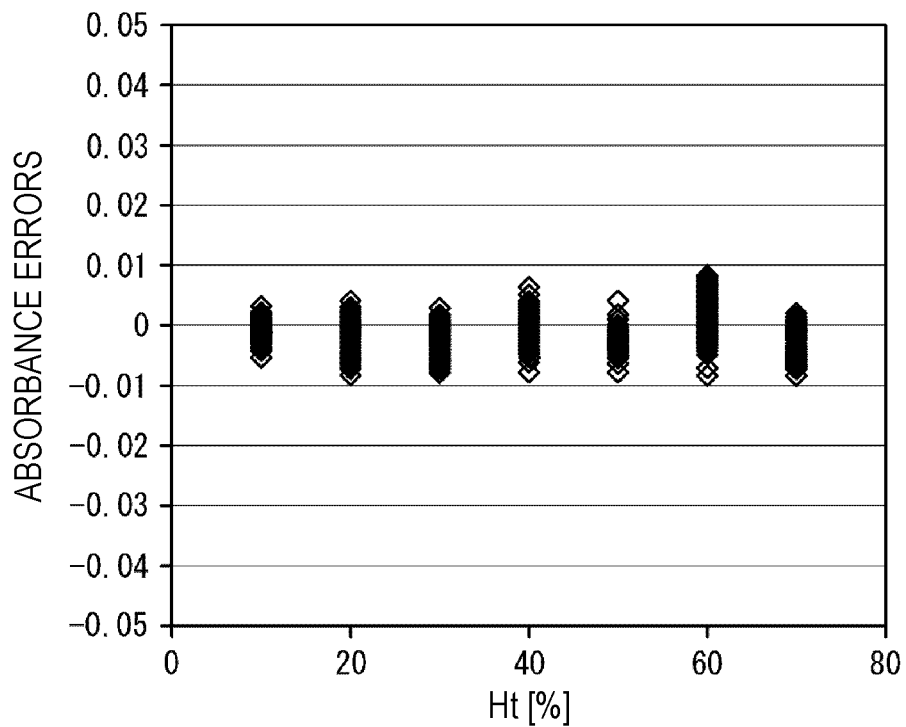
FIG. 15($a$) is a graph illustrating errors between absorbance measured by a component measurement method according to an embodiment and a true value, and FIG. 15($b$) is a graph illustrating errors between absorbance measured by a component measurement method according to Comparative Example and a true value.
Figure 15B:
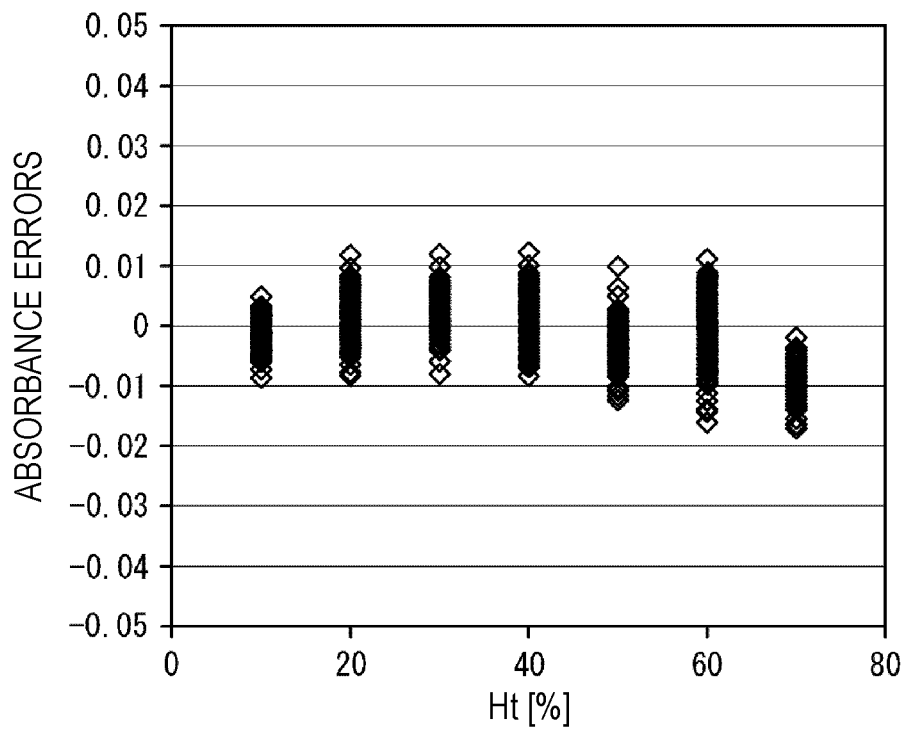

FIG. 15($a$) is a graph illustrating errors between calculated values of the noise absorbance at the measuring wavelength and actual values of the noise absorbance at the same measuring wavelength, where the calculated values were worked out by the component measurement method of the component measurement device 1, and, as mentioned above, the second predetermined wavelength $\lambda 2$ was 810 nm, the third predetermined wavelength $\lambda 3$ was 750 nm, the fourth predetermined wavelength $\lambda 4$ was 545 nm, and fifth predetermined wavelength $\lambda 5$ was 560 nm, and the first predetermined wavelength $\lambda 1$ serving as the measuring wavelength was 650 nm. In this Example, the absorbance of the color component contained in the whole absorbance at the third predetermined wavelength $\lambda 3$ is equivalent to 3% of the absorbance of the color component contained in the whole absorbance at the measuring wavelength. On the contrary, FIG. 15($b$) is a graph illustrating, as a comparative example, errors of calculated values of the noise absorbance at the measuring wavelength (650 nm) and actual values of the noise absorbance at the same measuring wavelength, where the calculated value was worked out by a similar method by using only two wavelengths of 810 nm and 750 nm among the second predetermined wavelength $\lambda 2$ to the fifth predetermined wavelength $\lambda 5$.

In the errors observed in FIG. 15($a$), 0.0058 is double the standard error, whereas 0.0109 is double the standard error in the errors observed in FIG. 15($b$) (not illustrated), indicating that the errors observed in FIG. 15($a$) are smaller than the errors observed in FIG. 15($b$). In other words, according to the component measurement method carried out by the component measurement device 1 of this embodiment, it is possible to estimate the absorbance of the color component at the measuring wavelength with higher accuracy than the case in which the absorbance is estimated from only the two wavelengths (810 nm and 750 nm in the verification experiments) within the long wavelength band W1. In this Example, when the hematocrit level is 40%, an absorbance error 0.001 corresponds to an error of 1 mg/dL in blood glucose level. Using the component measurement method, the component measurement device 1 is capable of reducing measurement errors in blood glucose level with respect to blood having a wide range of hematocrit levels from 10% to 70%.

Figure 16:
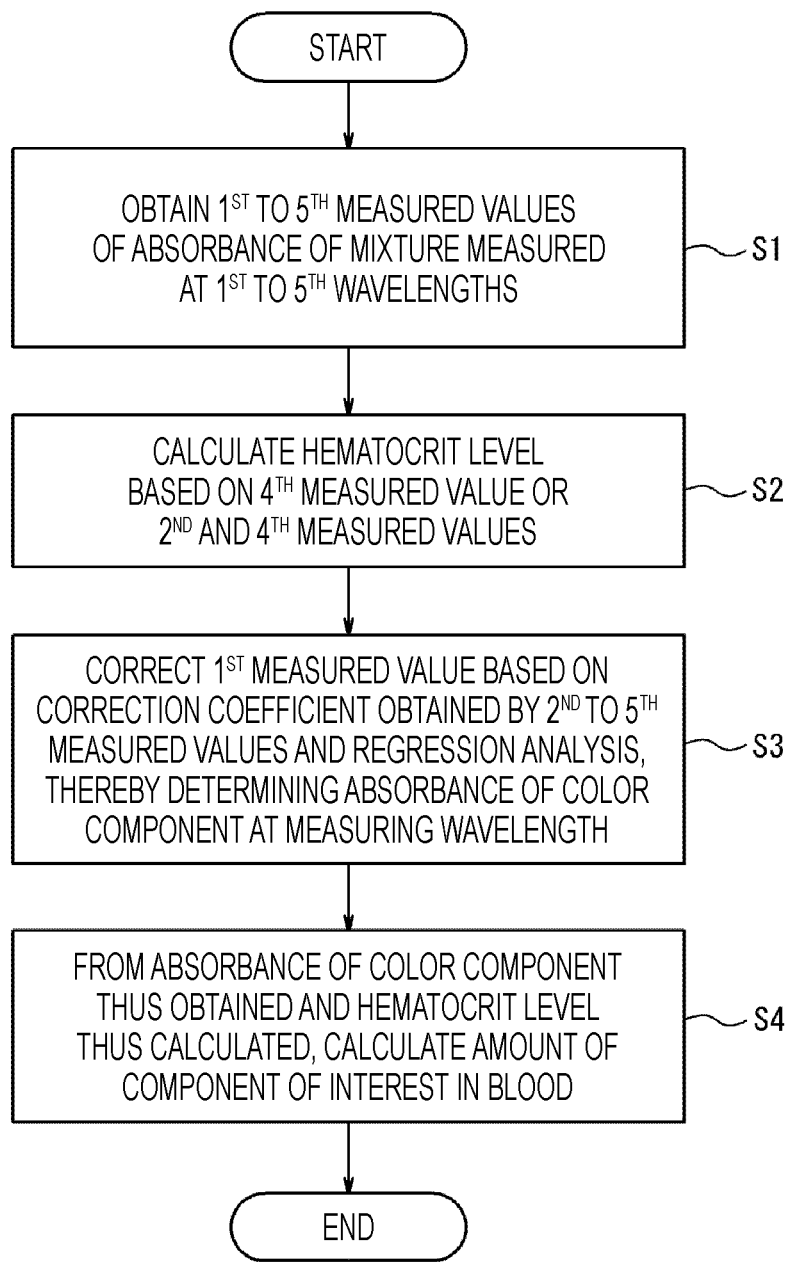
FIG. 16 is a flowchart illustrating the component measurement method according to an embodiment.

Finally, the component measurement method of the component measurement device 1 will be described with reference to FIG. 16. FIG. 16 is a flowchart illustrating the component measurement method carried out by the component measurement device 1.

This component measurement method includes step S1 of obtaining the first measured value D1, the second measured value D2, the third measured value D3, the fourth measured value D4, and the fifth measured value D5, where the first measured value D1 is the absorbance of the mixture X at the first predetermined wavelength $\lambda 1$ as the measuring wavelength, the second measured value D2 is the absorbance of the mixture X at the second predetermined wavelength $\lambda 2$, the third measured value D3 is the absorbance of the mixture X at the third predetermined wavelength $\lambda 3$, the fourth measured value D4 is the absorbance of the mixture X at the fourth predetermined wavelength $\lambda 4$, and the fifth measured value D5 is the absorbance of the mixture X at the fifth predetermined wavelength $\lambda 5$; step S2 of calculating a hematocrit level based on at least one of the first measured value D1 to the fifth measured value D5; step S3 of correcting the first measured value D1 based on the second measured value D2 to the fifth measured value D5 and correction coefficients obtained by regression calculation so as to obtain the absorbance of the color component at the first predetermined wavelength $\lambda 1$ as the measuring wavelength; and step S4 of calculating the component of interest in the blood from the absorbance of the color component at the first predetermined wavelength $\lambda 1$ as the measuring wavelength and the hematocrit level calculated.

In step S1, as described above, the first measured value D1 to the fifth measured value D5 are obtained with the light emitting unit 66 and the light receiving unit 72 of the measurement optical system 64. In this embodiment, in step S2, a hematocrit level is calculated based on the fourth measured value D4 or based on the fourth measured value D4 and the second measured value D2. Specifically, in step S2, the absorbance of hemoglobin is estimated from the fourth measured value D4 or from the fourth measured value D4 and the second measured value D2 so as to calculate a hematocrit level. Furthermore, when the fourth measured value D4 or the fourth measured value D4 and the second measured value D2 include absorption of the color component, the hematocrit level is calculated from a corrected value obtained by, for the fourth measured value D4 or for the fourth measured value D4 and the second measured value D2, correction calculation for subtracting an amount of absorption of the color component. In this embodiment, the hematocrit level is calculated from the calibration curve representing the relationship between the absorbance of hemoglobin and the hematocrit level in the mixture X, the calibration curve being stored in the memory 62. In step S3, the first measured value D1 is actually corrected based on the second measured value D2 to the fifth measured value D5 and the correction coefficients obtained by the regression calculation so as to estimate and obtain the absorbance of the color component at the measuring wavelength. Finally, in step S4, from the obtained absorbance of the color component at the first predetermined wavelength $\lambda 1$ as the measuring wavelength and from the hematocrit level thus calculated, a glucose concentration is worked out by using a calibration curve representing the relationship with the glucose concentration.

A case in which a measuring reagent 22 containing the other coloring reagent than the above-described coloring reagent was used. The above-described measuring reagent 22 was a mixed reagent containing glucose dehydrogenase (GDH), a tetrazolium salt (WST-4), and an electron mediator. In this case, the other coloring reagent contains, instead of the tetrazolium salt (WST-4), a tetrazolium salt A represented by [Chem. 1], where X=Na.

[Chem. 1]

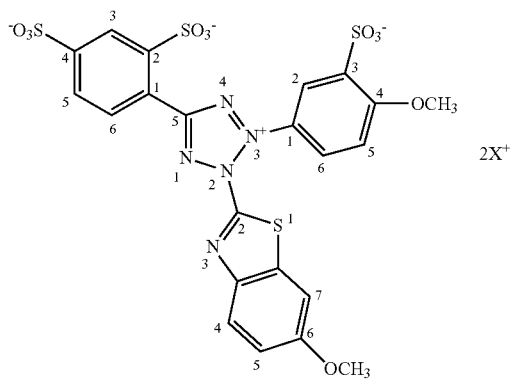

Figure 17:
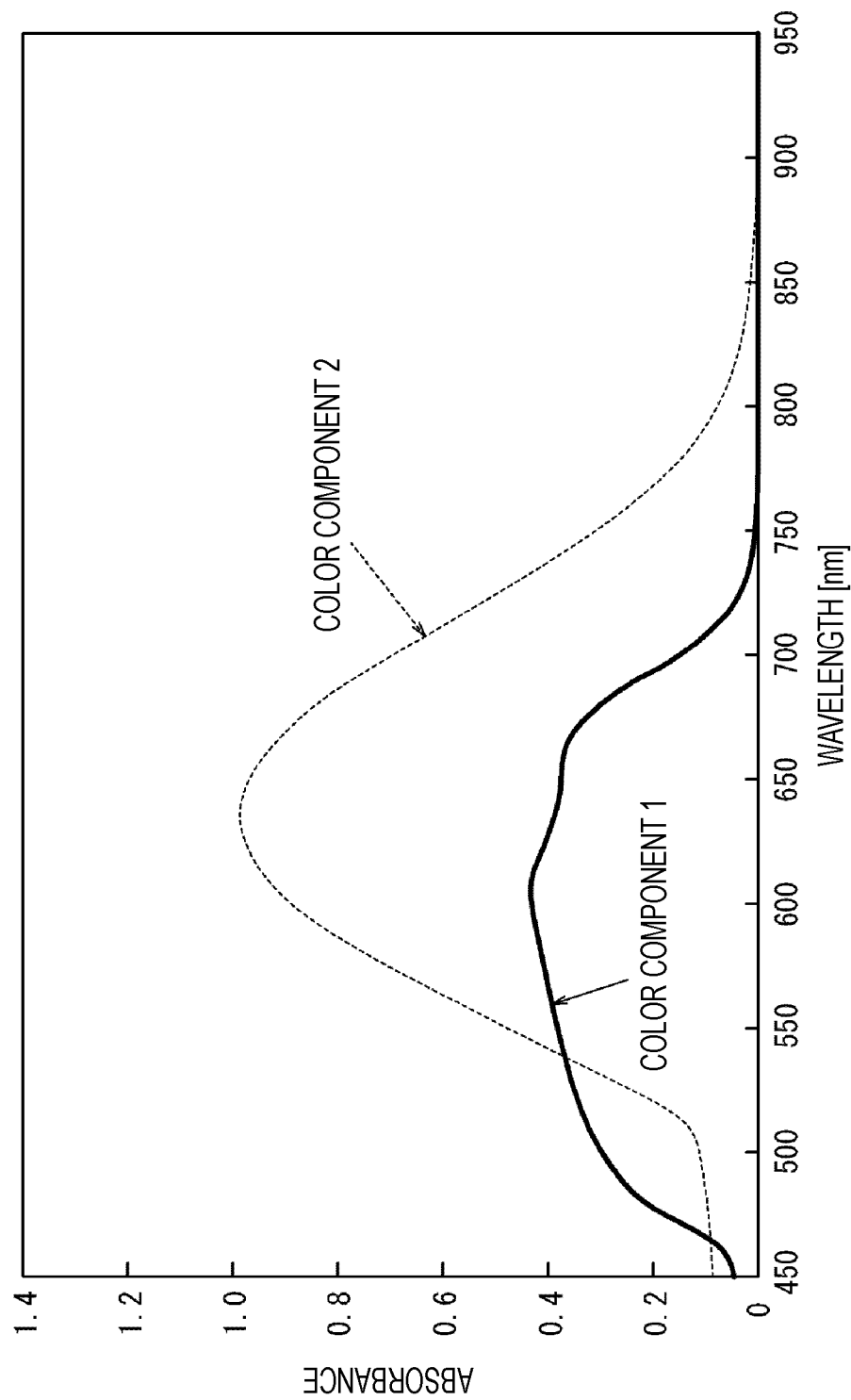
FIG. 17 is a graph illustrating absorbance spectra of two color components.

FIG. 17 is a graph illustrating absorbance spectrum of the color component (indicated as "color component 1" in FIG. 17) produced by the coloring reagent WST-4 contained in the above described measuring reagent 22, and absorbance spectrum of the color component (indicated as "color component 2" in FIG. 17) produced by the tetrazolium salt A, which was the coloring reagent contained in the measuring reagent 22 in this explanation, where these absorbance spectrums were measured with a sample of glucose water whose glucose concentration was 300 mg/dL.

As illustrated in FIG. 17, the absorbance spectrum of the color component of the tetrazolium salt A has an absorption peak that is much larger and much clear than the absorbance spectrum of the color component of WST-4. Therefore, compared with the case in which the absorption peak of the measuring reagent 22 containing WST-4 is used, the use of the absorption peak of the measuring reagent 22 containing the tetrazolium salt A further facilitates the detection of signals representing the absorbance of the color component, thereby making it possible to reduce errors in the measurement of the component of interest. Because the peak wavelength of the tetrazolium salt A is around 650 nm, it is possible to use 650 nm as the first predetermined wavelength $\lambda 1$ serving as the measuring wavelength, as in the above-described example. However, as illustrated in FIG. 17, the peak wavelength of the tetrazolium salt A is longer than the peak wavelength band of WST-4. Thus, if the same wavelength as the third predetermined wavelength $\lambda 3$ used in the above-described example was used, the light absorption of the tetrazolium salt A would largely influence the measurement of the component of interest, thereby making it easier for errors to occur in the measurement.

Therefore, if the measuring reagent 22 containing the tetrazolium salt A as the coloring reagent is used, it is so configured that a wavelength within a wavelength band insusceptible to the influence of the light absorption of the coloring reagent is used as the third predetermined wavelength $\lambda 3$. More specifically, the third predetermined wavelength $\lambda 3$ used in the case of using the measuring reagent 22 containing the tetrazolium salt A is a wavelength that belongs to the long wavelength band W1 such that absorbance of the color component contained in the whole absorbance at the third predetermined wavelength $\lambda 3$ is 10% or less, preferably 6% or less, more preferably 3% or less, or furthermore preferably substantially 0% of the color component contained in the whole absorbance at the measuring wavelength. Therefore, in this example, if the first predetermined wavelength $\lambda 1$ serving as the measuring wavelength is 650 nm, it is preferable to use a wavelength of 790 nm or more, it is more preferable to use a wavelength of 810 nm or more, it is furthermore preferable to use a wavelength of 830 nm or more, and it is especially preferable to use a wavelength of 920 nm or more.

However, in consideration of the characteristics of the general-purpose light sources such as LED elements actually used, the wavelength is preferably 950 nm or less, or more preferably 940 nm or less.

For the first predetermined wavelength $\lambda 1$, the second predetermined wavelength $\lambda 2$, the fourth predetermined wavelength $\lambda 4$, and the fifth predetermined wavelength $\lambda 5$, these predetermined wavelengths can be within respective wavelength bands similar to those described in the above-described example. By performing a component measurement method similar to the above-described example by using the first predetermined wavelength $\lambda 1$ to the fifth predetermined wavelength $\lambda 5$, it is possible to carry out correction suitable for the optical characteristics caused by the hemocyte in blood and the other causers, and for the ratio between the reduced hemoglobin and oxygenated hemoglobin in erythrocytes, thereby making it possible to attain measurement results with high accuracy.

Here, assuming that the measuring reagent 22 containing the tetrazolium salt A was used, regression analysis was carried out by using the equation [Math. 1] shown in the above-mentioned example, where the second predetermined wavelength $\lambda 2$ was 810 nm, the third predetermined wavelength $\lambda 3$ was 900 nm, the fourth predetermined wavelength $\lambda 4$ was 545 nm, and the fifth predetermined wavelength $\lambda 5$ was 560 nm on the basis on the selection criteria for the second predetermined wavelength $\lambda 2$ to the fifth predetermined wavelength $\lambda 5$. The regression analysis was carried out in a similar manner to that of the above-described example.

Figure 18:
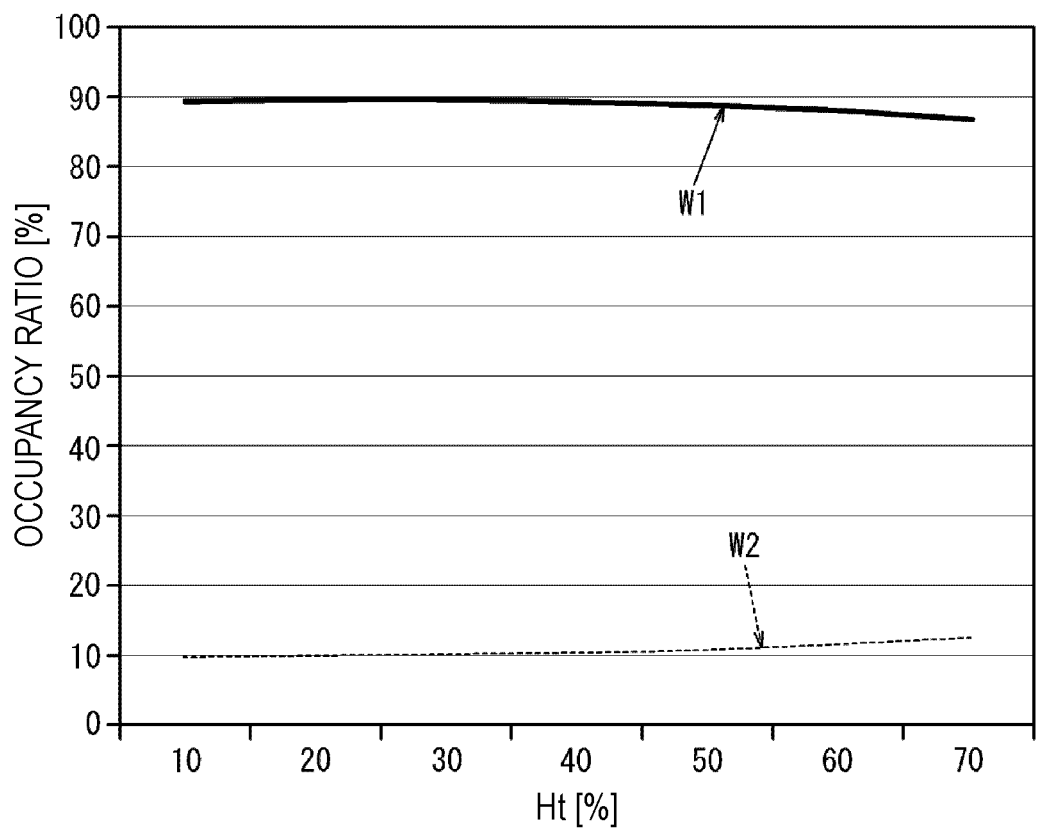
FIG. 18 is a graph illustrating an occupancy ratio of a long wavelength band and that of a short wavelength band within absorbance at a measurement wavelength, the absorbance being estimated by regression analysis as being caused by disturbance factor (noise) other than a color component.

FIG. 18 is a graph illustrating degree of influence (indicated as "W1" in FIG. 18) by the measured value in the long wavelength band W1 and degree of influence (indicated as "W2" in FIG. 18) by the measured value in the short wavelength band W2, the degrees of influence influencing the noise absorbance at the measuring wavelength in this regress calculation. The term "degree of influence" means the occupancy ratio in data as in the above. As illustrated in FIG. 18, the results of the measured data obtained by the regression calculation demonstrate that the results thus obtained are similar to the ones in the above-described example. More specifically, when the noise absorbance at the measuring wavelength is estimated by using the second measured value D2 to the fifth measured value D5, the second measured value D2 and the third measured value D3 respectively at the second predetermined wavelength λ2 and the third predetermined wavelength λ3 in the long wavelength band W1 reduce their degrees of influence from 90% to 88% as the hematocrit level increases from 10% to 70% (see "W1" in FIG. 18). On the other hand, the fourth measured value D4 and the fifth measured value D5 respectively at the fourth predetermined wavelength λ4 and the fifth predetermined wavelength λ5 in the short wavelength band W2 increase their degrees of influence from 10% to 12% as the hematocrit level increases from 10% to 70% (see "W2" in FIG. 18). These changes in the degrees of influence in the long wavelength band W1 and the short wavelength band W2 used depending on the hematocrit level make it possible to more accurately estimate the noise absorbance occurring at the measured wavelength, thereby consequently making it possible to more accurately estimate the absorbance of the color component at the measuring wavelength. If the second measured value D2 to the fifth measured value D5 included the absorbance of the color component, it would be necessary to perform correction calculation for the second measured value D2 to the fifth measured value D5, thereby working out the B (λ) that is the noise absorbance.

Next, results of validation experiment on accuracy of the estimation of the absorbance of the color component at the measuring wavelength are described, where the estimation was such that the coloring reagent containing the tetrazolium salt A was used, and the estimation was on the basis of the optical characteristics of the hemocyte in blood and the other causers and the ratio between the reduced hemoglobin and oxygenated hemoglobin in erythrocytes. The samples (n=766) were prepared by adjusting the hematocrit levels of the blood to 10%, 20%, 30%, 40%, 50%, 60%, and 70%.

Figure 19A:
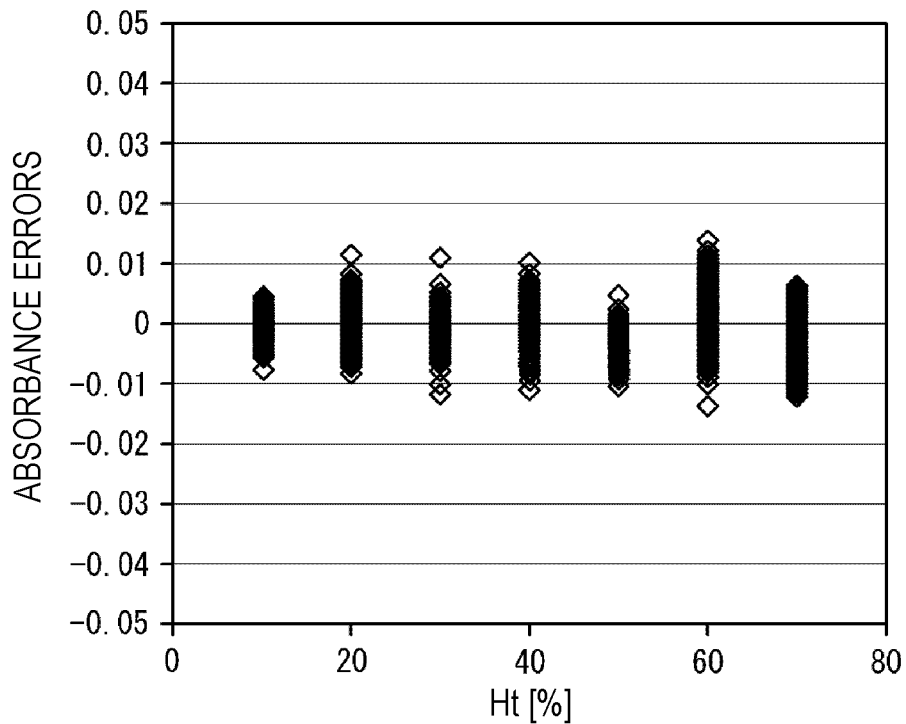
FIG. 19(a) is a graph illustrating errors between absorbance measured by a component measurement method according to an embodiment and a true value.

FIG. 19(a) is a graph illustrating errors between calculated values of noise absorbance at the measuring wavelength and the actual values of the noise absorbance at the same measuring wavelength, where the calculated value was worked out by the component measurement method of the component measurement device 1, where, as mentioned above, the second predetermined wavelength λ2 was 810 nm, the third predetermined wavelength λ3 was 900 nm, the fourth predetermined wavelength λ4 was 545 nm, the fifth predetermined wavelength λ5 was 560 nm, and the first predetermined wavelength λ1 serving as the measuring wavelength was 650 nm. In this Example, the absorbance of the color component contained in the whole absorbance in the third predetermined wavelength λ3 is equivalent to 1% of the absorbance contained in the whole absorbance at the measuring wavelength. On the other hand, FIG. 19(b) is a graph illustrating, as a comparative example, errors between calculated values of the noise absorbance at the measuring wavelength (650 nm) and actual values of the noise absorbance at the same measuring wavelength, where the calculated values are worked out by a similar method except that only two wavelengths of 810 nm and 900 nm were used among the second predetermined wavelength λ2 to the fifth predetermined wavelength λ5.

Figure 19B:
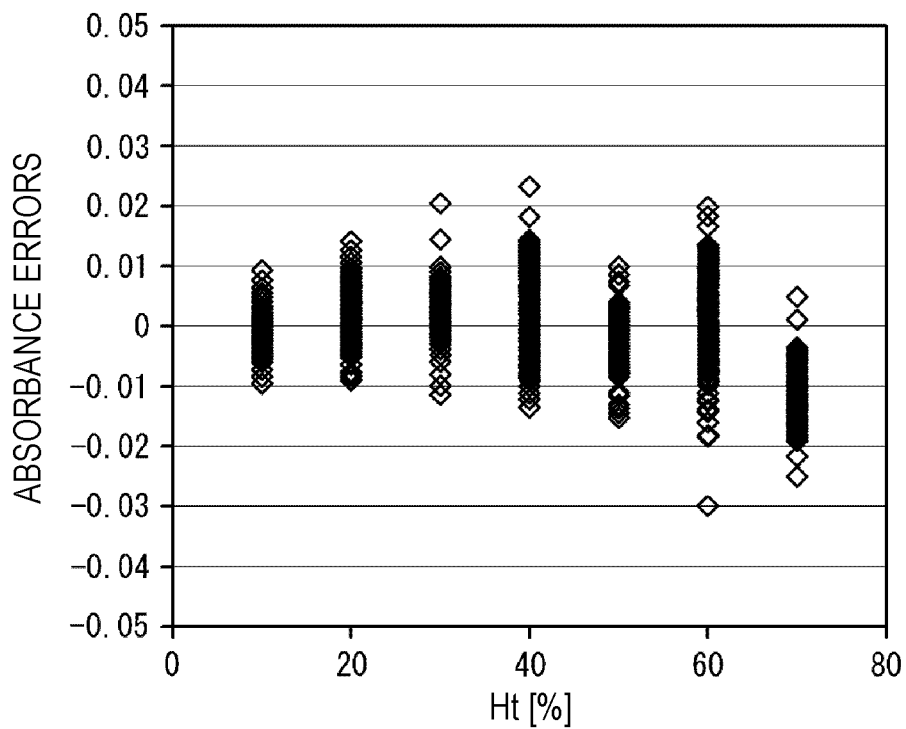
FIG. 19(b) is a graph illustrating errors between absorbance measured by a component measurement method according to Comparative Example and a true value.

The errors observed in FIG. 19(a) are such that 0.0085 is double the standard error, while the errors observed in FIG. 19(b) are such that 0.0140 is double the standard error (not illustrated). This demonstrates that the errors observed in FIG. 19(a) are smaller than those observed in FIG. 19(b). That is, regardless of the kinds of the coloring reagent, the component measurement method performed with the component measurement device 1 makes it possible to estimate the absorbance with higher accuracy than the absorbance of the color component measured at the measuring wavelength and estimated only from two wavelengths in the long wavelength band W1 (810 nm and 900 nm in this validation experiment). In this example, when the hematocrit level is 40%, absorbance error of 0.002 is equivalent to blood glucose level of 1 [mg/dL]. Using the component measurement method, the component measurement device 1 is capable of reducing measurement errors in blood glucose level with respect to blood having a wide range of hematocrit levels from 10% to 70%.

As described above, the third predetermined wavelength λ3 used in this Example was 900 nm belonging to a wavelength band longer than 750 nm of the third predetermined wavelength λ3 used in the above-described example. Therefore, the value of the third predetermined wavelength λ3 for use in the case of using the measuring reagent 22 containing the tetrazolium salt A is more distanced from 650 nm of the measuring wavelength, compared with the value of the third predetermined wavelength λ3 for use in the case of using the measuring reagent 22 containing WST-4, and therefore, is more disadvantageous in terms of measurement errors in view of this. However, as illustrated in FIG. 17, the tetrazolium salt A has a large absorption peak than that of WST-4, thereby facilitating the detection of the signals representing the absorbance of the color component. The strength of the signals also helps to reduce the increase of the measurement errors caused due to the longer distance between the third predetermined wavelength λ3 and the measuring wavelength. As a result, even if a third predetermined wavelength λ3 more distanced from the measuring wavelength is used, the errors in the measurement of the component of interest can be reduced.

The component measurement device and the component measurement device set according to the present disclosure are not limited to the specific descriptions of the embodiment above, and may be modified in various ways within the gist of the invention recited in Claims. The component measurement device and the component measurement device set according to the present invention are not limited to the measurement of concentration and may be configured to measure the other physical properties than concentration, while the glucose concentration measurement measuring glucose as the component of interest is exemplified in the embodiments. Furthermore, the embodiments exemplify the case in which the component of interest in blood to measure is glucose in plasma component, but the component of interest to measure is not limited to this, and may be cholesterol, sugars, ketone body, uric acid, hormones, nucleic acids, antibodies, antigens and the like in blood, for example. Therefore, the component measurement device is not limited to a blood glucose level measurement device. Furthermore, while the embodiments adopt the light receiving unit 72 for receiving the transmitted light that has been transmitted through the component measurement chip 2, a light receiving unit for receiving reflected light reflected from the component measurement chip 2 may be adopted. The embodiments are described as measuring the blood glucose level in the whole blood without including a step of separating blood, but may be configured to measure blood that have been filtered to remove part of the hemocyte component or the dust and the like, or to measure blood that have been subjected to hemolysis in the chip 2 by using a reagent for dissolving hemocytes. The separation of blood may be not to filter the blood but separate into portions of whole blood, so that the portions thus divided can be supplied to a measuring area for the reaction with the measuring reagent 22 and to a correction area for the correction, and the calculations are carried out for the respective areas.

The present disclosure relates to a component measurement device and a component measurement device set.

REFERENCE NUMERAL LIST

1 Component measurement device
2 Component measurement chip
3 Housing
10*a* Main body
10*b* Chip attaching portion
11 Display unit
12 Detachment lever
13 Power button
14 Operation button
21 Base member
22 Measuring reagent (reagent)
23 Flow path
23*a* Space
24 Supplying section
25 Cover member
26 Ejector pin
60 Computing unit
62 Memory
63 Power supply circuit
64 Measurement optical system
66 Light emitting unit
67 First light source
68*a* Second light source
68*b* Third light source
68*c* Fourth light source
68*d* Fifth light source
69*a* First diaphragm unit
69*b* Second diaphragm unit
70 Light emission control circuit
72 Light receiving unit
74 Light reception control circuit
76 Measurement instruction unit
77 Concentration measurement unit
78 Absorbance obtaining unit
80 Holder member
84 Absorbance correction unit
85 Measured value data
86 Correction coefficient data
90 Calibration curve data
100 Component measurement device set
D1 First measured value
D2 Second measured value
D3 Third measured value
D4 Fourth measured value
D5 Fifth measured value
S Chip attaching space
SL1 to SL5 Radiation position of light source
T1 Distance between light source and first diaphragm unit
T2 Distance between light source and light receiving unit
T3 Distance between mixture and first diaphragm unit
T4 Distance between light source and second diaphragm unit
W1 Long wavelength band
W2 Short wavelength band
W3 Wavelength band corresponding to full width at half maximum
X Mixture $\Lambda$1 First predetermined wavelength
$\Lambda$2 Second predetermined wavelength
$\Lambda$3 Third predetermined wavelength
$\Lambda$4 Fourth predetermined wavelength
$\Lambda$5 Fifth predetermined wavelength

The invention claimed is:

1. A component measurement device for measuring a component of interest in blood on a basis of optical characteristics of a mixture containing a color component produced by a color reaction between the component of interest in the blood and a reagent, the component measurement device comprising:
   a flow path configured to allow the blood to flow in a flow direction;
   a first light source configured to emit first irradiation light of a first predetermined wavelength to the mixture;
   a second light source configured to emit second irradiation light of a second predetermined wavelength to the mixture, the second irradiation light to be used for estimation of a noise amount contained in a measured value of absorbance of the mixture measured by using the first irradiation light of the first light source, the noise amount being derived other than from the color component;
   a third light source configured to emit third irradiation light of a third predetermined wavelength to the mixture, the third irradiation light to be used for estimation of the noise amount; and
   a fourth light source configured to emit fourth irradiation light of a fourth predetermined wavelength to the mixture, the fourth irradiation light to be used for estimation of the noise amount;
   wherein the first light source, the second light source, and the third light source are aligned in a flow path width direction perpendicular to the flow direction of the blood at a position where the mixture is present in the flow path of the blood;
   wherein the first predetermined wavelength of the first light source is not less than 600 nm and not more than 700 nm;
   wherein the second predetermined wavelength of the second light source is longer than the first predetermined wavelength of the first light source;
   wherein the fourth predetermined wavelength of the fourth light source is shorter than the first predetermined wavelength of the first light source;
   wherein the first light source is configured to irradiate the first irradiation light to the mixture at a first irradiation position, and the second light source is configured to irradiate the second irradiation light to the mixture at a second irradiation position; and
   wherein the first irradiation position and the second irradiation position at least partially overlap with each other in the flow path width direction.

2. The component measurement device according to claim 1,
   wherein the first light source is positioned between the second light source and the third light source.

3. The component measurement device according to claim 1, wherein:
   the third light source is configured to irradiate the third irradiation light to the mixture at a third irradiation position; and
   the first irradiation position and the third irradiation position at least partially overlap with each other in the flow path width direction.

4. The component measurement device according to claim 3, wherein:
the second irradiation position and the third irradiation position at least partially overlap with each other in the flow path width direction.

5. The component measurement device according to claim 1, wherein the first light source and the fourth light source are aligned in the flow direction.

6. The component measurement device according to claim 1, further comprising:
a fifth light source configured to emit fifth irradiation light of a fifth predetermined wavelength to the mixture, the fifth irradiation light to be used for the estimation of the noise amount;
wherein the first light source, the fourth light source, and the fifth light source are aligned in the flow direction with the first light source positioned between the fourth light source and the fifth light source.

7. The component measurement device according to claim 1, further comprising:
a light receiving unit positioned to face the first light source and the second light source with the mixture between the light receiving unit and the first and second light sources when the mixture is present in the flow path, the light receiving unit being configured to receive transmitted light, which is a part of the first and second irradiation light that has been transmitted through the mixture; and
a diaphragm unit positioned between the mixture and the light receiving unit, and configured to control how much of the transmitted light that was transmitted through the mixture reaches the light receiving unit.

8. The component measurement device according to claim 7, wherein the diaphragm unit is referred to as a first diaphragm unit, and
the component measurement device further comprises a second diaphragm unit positioned to be between the mixture and the first and second light sources, and configured to control how much of the first irradiation light and the second irradiation light reaches the mixture from the first light source and the second light source.

9. A component measurement device set, comprising:
a component measurement chip that defines a flow path for a flow of blood in a flow direction, and that is provided with a reagent in the flow path, the reagent containing a coloring reagent for causing a color reaction with a component of interest in the blood so as to produce a color component; and
a component measurement device configured to receive the component measurement chip, and to measure the component of interest in the blood on a basis of optical characteristics of a mixture containing the color component produced in the flow path by the color reaction, the component measurement device comprising:
a first light source configured to emit first irradiation light of a first predetermined wavelength to the mixture in the flow path of the component measurement chip attached to the component measurement device;
a second light source configured to emit second irradiation light of a second predetermined wavelength to be emitted to the mixture in the flow path of the component measurement chip attached to the component measurement device, the second irradiation light to be used for estimation of a noise amount contained in a measured value of absorbance of the mixture measured by using the first irradiation light of the first light source, the noise amount being derived other than from the color component;
a third light source configured to emit third irradiation light of a third predetermined wavelength to the mixture, the third irradiation light to be used for estimation of the noise amount; and
a fourth light source configured to emit fourth irradiation light of a fourth predetermined wavelength to the mixture, the fourth irradiation light to be used for estimation of the noise amount;
wherein the first light source, the second light source, and the third light source are aligned in a flow path width direction perpendicular to the flow direction of the blood at a position where the mixture is present in the flow path of the component measurement chip attached to the component measurement device;
wherein the first light source and the fourth light source are aligned in the flow direction;
wherein the first predetermined wavelength of the first light source is not less than 600 nm and not more than 700 nm;
wherein the second predetermined wavelength of the second light source is longer than the first predetermined wavelength of the first light source;
wherein the fourth predetermined wavelength of the fourth light source is shorter than the first predetermined wavelength of the first light source;
wherein the first light source is configured to irradiate the first irradiation light to the mixture at a first irradiation position, and the second light source is configured to irradiate the second irradiation light to the mixture at a second irradiation position; and
wherein the first irradiation position and the second irradiation position at least partially overlap with each other in the flow path width direction.

10. The component measurement device set according to claim 9, wherein the component measurement chip is detachable from the component measurement device.

11. A method for measuring a component of interest in blood, the method comprising:
providing a component measurement chip that defines a flow path for a flow of the blood in a flow direction, and that is provided with a reagent in the flow path, the reagent containing a coloring reagent for causing a color reaction with a component of interest in the blood so as to produce a color component;
providing a component measurement device configured to receive the component measurement chip, and to measure the component of interest in the blood on a basis of optical characteristics of a mixture containing the color component produced in the flow path by the color reaction, the component measurement device comprising:
a first light source configured to emit first irradiation light of a first predetermined wavelength to the mixture in the flow path of the component measurement chip attached to the component measurement device; and
a second light source configured to emit second irradiation light of a second predetermined wavelength to be emitted to the mixture in the flow path of the component measurement chip attached to the component measurement device,
a third light source configured to emit third irradiation light of a third predetermined wavelength to the mixture in the flow path of the component measurement chip attached to the component measurement device; and a fourth light source configured to emit fourth irradiation light of a fourth predetermined wavelength to the mixture in the flow path of the component measurement chip attached to the component measurement device;

wherein the first light source, the second light source, and the third light source are aligned in a flow path width direction perpendicular to the flow direction of the blood at a position where the mixture is present in the flow path of the component measurement chip attached to the component measurement device;

wherein the first light source and the fourth light source are aligned in the flow direction;

wherein the first predetermined wavelength of the first light source is not less than 600 nm and not more than 700 nm;

wherein the second predetermined wavelength of the second light source is longer than the first predetermined wavelength of the first light source;

wherein the fourth predetermined wavelength of the fourth light source is shorter than the first predetermined wavelength of the first light source;

wherein the first light source is configured to irradiate the first irradiation light to the mixture at a first irradiation position, and the second light source is configured to irradiate the second irradiation light to the mixture at a second irradiation position; and wherein the first irradiation position and the second irradiation position at least partially overlap with each other in the flow path width direction; and using the second irradiation light, the third irradiation light, and the fourth irradiation light to estimate a noise amount contained in a measured value of absorbance of the mixture measured by using the first irradiation light of the first light source, the noise amount being derived other than from the color component.

* * * * *